(12) United States Patent
Thieberger et al.

(10) Patent No.: US 12,379,778 B2
(45) Date of Patent: Aug. 5, 2025

(54) SMART WINDOWING FOR REDUCING POWER CONSUMPTION OF A HEAD-MOUNTED CAMERA USED FOR DETECTING FACIAL EXPRESSIONS

(71) Applicant: Facense Ltd., Kiryat Tivon (IL)

(72) Inventors: Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 18/627,695

(22) Filed: Apr. 5, 2024

(65) Prior Publication Data

US 2024/0256038 A1 Aug. 1, 2024

Related U.S. Application Data

(63) Continuation of application No. 18/105,829, filed on Feb. 4, 2023, now Pat. No. 11,983,317, which is a (Continued)

(51) Int. Cl.
*G06F 3/13* (2006.01)
*A61B 5/00* (2006.01)
(Continued)

(52) U.S. Cl.
CPC .......... *G06F 3/013* (2013.01); *A61B 5/0205* (2013.01); *A61B 5/02427* (2013.01);
(Continued)

(58) Field of Classification Search
CPC ...... G06F 3/13; G06V 40/174; G06V 10/141; G06V 40/166; H04N 23/651;
(Continued)

(56) References Cited

U.S. PATENT DOCUMENTS 8,270,473 B2 9/2012 Chen et al.
8,401,248 B1 3/2013 Moon et al.
(Continued)

FOREIGN PATENT DOCUMENTS

JP WO2017006872 12/2017

OTHER PUBLICATIONS

U.S. Appl. No. 10/074,024, filed Sep. 11, 2018, el Kaliouby et al.
(Continued)

*Primary Examiner* — Nguyen T Truong
(74) *Attorney, Agent, or Firm* — Active Knowledge Ltd.

(57) ABSTRACT

System and method that utilize windowing for efficient capturing of facial landmarks include an inward-facing head-mounted camera that captures images of a region on a user's face utilizing a sensor supporting changing of its region of interest (ROI). The system also includes a computer that detects, based on the images, a type of facial expression expressed by the user, which belongs to a group comprising first and second facial expressions. Responsive to detecting that the user expresses the first facial expression, the computer reads from the camera a first ROI that covers a first subset of facial landmarks relevant to the first facial expression. Responsive to detecting that the user expresses the second facial expression, the computer reads from the camera a second ROI that covers a second subset of facial landmarks relevant to the second facial expression, with the first and second ROIs being different.

20 Claims, 7 Drawing Sheets

Related U.S. Application Data continuation of application No. 17/524,411, filed on Nov. 11, 2021, now Pat. No. 11,604,511.

(60) Provisional application No. 63/140,453, filed on Jan. 22, 2021, provisional application No. 63/122,961, filed on Dec. 9, 2020, provisional application No. 63/113,846, filed on Nov. 14, 2020.

(51) Int. Cl.
| | |
|---|---|
| A61B 5/0205 | (2006.01) |
| A61B 5/024 | (2006.01) |
| A61B 5/145 | (2006.01) |
| A61B 5/1455 | (2006.01) |
| G06F 3/01 | (2006.01) |
| G06V 10/141 | (2022.01) |
| G06V 40/16 | (2022.01) |
| H04N 23/611 | (2023.01) |
| H04N 23/65 | (2023.01) |
| H04N 23/951 | (2023.01) |
| H04N 25/46 | (2023.01) |

(52) U.S. Cl.
CPC ...... *A61B 5/02438* (2013.01); *A61B 5/14546* (2013.01); *A61B 5/1455* (2013.01); *A61B 5/6803* (2013.01); *G06V 10/141* (2022.01); *G06V 40/166* (2022.01); *G06V 40/174* (2022.01); *H04N 23/611* (2023.01); *H04N 23/651* (2023.01); *H04N 23/951* (2023.01); *A61B 5/02416* (2013.01); *A61B 5/7221* (2013.01); *H04N 25/46* (2023.01)

(58) Field of Classification Search
CPC .. H04N 23/951; H04N 23/611; A61B 5/0205; A61B 5/02427; A61B 5/02438
USPC .......................................................... 348/77
See application file for complete search history.

(56) References Cited

U.S. PATENT DOCUMENTS

| 9,836,484 B1 | 12/2017 | Bialynicka-Birula et al. |
|---|---|---|
| 2017/0007165 A1* | 1/2017 | Jain ........................ A61B 5/165 |
| 2018/0137678 A1 | 5/2018 | Kaehler |

OTHER PUBLICATIONS

U.S. Appl. No. 10/335,045, filed Jul. 2, 2019, Sebe et al.
U.S. Appl. No. 10/665,243, filed May 26, 2020, Whitmire et al.
Al Chanti, Dawood and Alice Caplier. "Spontaneous facial expression recognition using sparse representation." arXiv preprint arXiv:1810. 00362 (2018).
Barrett, Lisa Feldman, et al. "Emotional expressions reconsidered: Challenges to inferring emotion from human facial movements." Psychological science in the public interest 20.1 (2019): 1-68.
Canedo, Daniel, and António JR Neves. "Facial expression recognition using computer vision: a systematic review." Applied Sciences 9.21 (2019): 4678.
Cha, Jaekwang, Jinhyuk Kim, and Shiho Kim. "Hands-free user interface for AR/VR devices exploiting wearer's facial gestures using unsupervised deep learning." Sensors 19.20 (2019): 4441.
Chew, Sien W., et al. "Sparse temporal representations for facial expression recognition." Pacific-Rim Symposium on Image and Video Technology. Springer, Berlin, Heidelberg, 2011.
Corneanu, Ciprian Adrian, et al. "Survey on rgb, 3d, thermal, and multimodal approaches for facial expression recognition: History, trends, and affect-related applications." IEEE transactions on pattern analysis and machine intelligence 38.8 (2016): 1548-1568.
Gao, Xinbo, et al. "A review of active appearance models." IEEE Transactions on Systems, Man, and Cybernetics, Part C (Applications and Reviews) 40.2 (2010): 145-158.
Hickson, Steven, et al. "Eyemotion: Classifying facial expressions in VR using eye-tracking cameras." 2019 IEEE Winter Conference on Applications of Computer Vision (WACV). IEEE, 2019.
Jia, Shan, et al. "Detection of Genuine and Posed Facial Expressions of Emotion: Databases and Methods." Frontiers in Psychology 11 (2020): 3818.
Kerst, Ariane, Jürgen Zielasek, and Wolfgang Gaebel. "Smartphone applications for depression: a systematic literature review and a survey of health care professionals' attitudes towards their use in clinical practice." European archives of psychiatry and clinical neuroscience 270.2 (2020): 139-152.
Li, Hao, et al. "Facial performance sensing head-mounted display." ACM Transactions on Graphics (ToG) 34.4 (2015): 1-9.
Li, Shan, and Weihong Deng. "Deep facial expression recognition: A survey." IEEE transactions on affective computing (2020).
Masai, Katsutoshi, et al. "Evaluation of facial expression recognition by a smart eyewear for facial direction changes, repeatability, and positional drift." ACM Transactions on Interactive Intelligent Systems (TiiS) 7.4 (2017): 1-23.
Masai, Katsutoshi, Yuta Sugiura, and Maki Sugimoto. "Facerubbing: Input technique by rubbing face using optical sensors on smart eyewear for facial expression recognition." Proceedings of the 9th Augmented Human International Conference. 2018.
Masai, Katsutoshi. "Facial Expression Classification Using Photoreflective Sensors on Smart Eyewear.", PhD Thesis, (2018).
Milborrow, Stephen, and Fred Nicolls. "Locating facial features with an extended active shape model." European conference on computer vision. Springer, Berlin, Heidelberg, 2008.
Nakamura, Fumihiko, et al. "Automatic Labeling of Training Data by Vowel Recognition for Mouth Shape Recognition with Optical Sensors Embedded in Head-Mounted Display." ICAT-EGVE. 2019.
Nakamura, Hiromi, and Homei Miyashita. "Control of augmented reality information volume by glabellar fader." Proceedings of the 1st Augmented Human international Conference. 2010.
Perusquía-Hernández, Monica. "Are people happy when they smile?: Affective assessments based on automatic smile genuineness identification." Emotion Studies 6.1 (2021): 57-71.
Ringeval, Fabien, et al. "AVEC 2019 workshop and challenge: state-of-mind, detecting depression with AI, and cross-cultural affect recognition." Proceedings of the 9th International on Audio/Visual Emotion Challenge and Workshop. 2019.
Si, Jiaxin, Yanchen Wan, and Teng Zhang. "Facial expression recognition based on ASM and Finite Automata Machine." (2016): 1306-1310. Proceedings of the 2016 2nd Workshop on Advanced Research and Technology in Industry Applications.
Sugiura, Yuta, et al. "Behind the palm: Hand gesture recognition through measuring skin deformation on back of hand by using optical sensors." 2017 56th Annual Conference of the Society of Instrument and Control Engineers of Japan (SICE). IEEE, 2017.
Suk, Myunghoon, and Balakrishnan Prabhakaran. "Real-time facial expression recognition on smartphones." 2015 IEEE Winter Conference on Applications of Computer Vision. IEEE, 2015.
Suzuki, Katsuhiro, et al. "Recognition and mapping of facial expressions to avatar by embedded photo reflective sensors in head mounted display." 2017 IEEE Virtual Reality (VR). IEEE, 2017.
Terracciano, Antonio, et al. "Personality predictors of longevity: activity, emotional stability, and conscientiousness." Psychosomatic medicine 70.6 (2008): 621.
Umezawa, Akino, et al. "e2-MaskZ: a Mask-type Display with Facial Expression Identification using Embedded Photo Reflective Sensors." Proceedings of the Augmented Humans International Conference. 2020.
Valstar, Michel, et al. "Avec 2016: Depression, mood, and emotion recognition workshop and challenge." Proceedings of the 6th international workshop on audio/visual emotion challenge. 2016.
Yamashita, Koki, et al. "CheekInput: turning your cheek into an input surface by embedded optical sensors on a head-mounted display." Proceedings of the 23rd ACM Symposium on Virtual Reality Software and Technology. 2017.

(56) References Cited

OTHER PUBLICATIONS

Yamashita, Koki, et al. "DecoTouch: Turning the Forehead as Input Surface for Head Mounted Display." International Conference on Entertainment Computing. Springer, Cham, 2017.

Zeng, Nianyin, et al. "Facial expression recognition via learning deep sparse autoencoders." Neurocomputing 273 (2018): 643-649.

* cited by examiner

Facial Expression: Neutral
Read Bitrate: Low

Facial Expression: Non-Neutral
Read Bitrate: High

VS.

Angry Expression     Happy Expression

☐ Relevant Region
⌐ ¬ Less relevant region

SMART WINDOWING FOR REDUCING POWER CONSUMPTION OF A HEAD-MOUNTED CAMERA USED FOR DETECTING FACIAL EXPRESSIONS

CROSS-REFERENCE TO RELATED APPLICATIONS

This Application is a Continuation of U.S. application Ser. No. 18/105,829, filed Feb. 4, 2023, which is a Continuation of U.S. application Ser. No. 17/524,411, filed Nov. 11, 2021. U.S. application Ser. No. 17/524,411 claims priority to U.S. Provisional Patent Application No. 63/113,846, filed Nov. 14, 2020, U.S. Provisional Patent Application No. 63/122, 961, filed Dec. 9, 2020, and U.S. Provisional Patent Application No. 63/140,453 filed Jan. 22, 2021.

BACKGROUND

Tracking facial expressions is becoming an important feature of head-mounted systems, such as augmented reality and virtual reality headsets. These devices often include non-contact head-mounted electro-optical sensors, such as cameras or photosensor-based devices, which take measurements of the face from which facial expressions can be determined. Facial expressions data can be used for many applications such as rendering facial expressions on real-time avatars or determining a user's momentary emotional response.

Often there is a need to perform facial expression tracking over long periods of time, while the user performs day-to-day operations. This often involves utilization of head-mounted systems that are untethered and battery-operated. However, the collection and processing of the measurements collected in such scenarios can require substantial power from the limited supply available with battery-operated devices. Thus, there is a need for a way to increase the efficiency of collection of data involved in detection of facial expressions.

SUMMARY

Some aspects of this disclosure involve light-weight systems that use power-efficient detection of facial expressions. This makes these systems suitable for use with untethered, head-mounted systems such as systems with AR/VR head-mounted displays (HMDs). When tracking facial expressions, not all the regions on the face carry the same importance, some regions are more informative and other regions are less informative. Therefore, in some embodiments, a region of interest (ROI) of a camera used for facial expression tracking is set around the more informative regions, in order to save power, reduce computations, and/or optimize its performances.

One aspect of this disclosure involves a system that utilizes windowing (of a camera sensor) for efficient capturing of facial landmarks includes an inward-facing head-mounted camera and a computer. The camera capture images of a region on a user's face utilizing a sensor that supports changing of its region of interest (ROI). The computer detects, based on the images, a type of facial expression expressed by the user, which belongs to a group comprising first and second facial expressions. Responsive to detecting that the user expresses the first facial expression, the computer reads from the camera a first ROI that covers a first subset of facial landmarks relevant to the first facial expression. Responsive to detecting that the user expresses the second facial expression, the computer reads from the camera a second ROI that covers a second subset of facial landmarks relevant to the second facial expression, with the first and second ROIs being different.

In one example, the computer selects the first subset as follows: the computer calculates first relevance scores for facial landmarks extracted from a first subset of the images, selects a first proper subset of the facial landmarks whose relevance scores reach a first threshold, and sets the first ROI to cover the first proper subset of the facial landmarks. Optionally, the computer selects the second subset as follows: the computer calculates second relevance scores for facial landmarks extracted from a second subset of the images, select a second proper subset of the facial landmarks whose relevance scores reach a second threshold, and sets the second ROI to cover the second proper subset of the facial landmarks.

In one embodiment, each of the first and second ROIs covers less than half of the region and the computer detects changes in locations of the facial landmarks in the first and second subsets due to facial movements and/or movements of the camera relative to the face, and updates each of the first and second ROIs according to the changes.

In one embodiment, the sensor supports at least two different binning values for at least two different ROIs, respectively, and the computer (i) selects, based on performance metrics of facial expression analysis configured to detect the type of facial expression expressed by the user, first and second resolutions for the first and second ROIs, respectively, and (ii) sets different binning values for the first and second ROIs according to the first and second resolutions.

In one embodiment, the sensor supports changing its binning value, and the computer calculates relevance scores for facial landmarks extracted from overlapping sub-regions having at least two different binning values. Optionally, the sub-regions are subsets of the region, and a relevance score per facial landmark at a binning value increases as accuracy of facial expression detection based on the facial landmark at the binning value increases and power consumption used for the facial expression detection decreases. Optionally, the computer sets the binning values according to a function that optimizes the relevance scores.

In one embodiment, the camera is physically coupled to a frame configured to be worn on the user's head, the camera is located less than 15 cm away from the user's face, and the computer renders an avatar of the user based on data read from the camera. Optionally, the system reduces power consumption of its head-mounted components by checking quality of predictions of locations of facial landmarks using a model, and if the locations of the facial landmarks are closer than a threshold to their expected locations, then a bitrate at which the camera is read is reduced. Optionally, the computer identifies that the locations of the facial landmarks are not closer than the threshold to their expected locations, and then increases the bitrate at which the camera is read.

Another aspect of this disclosure is a method that includes at least the following steps: capturing images of a region on a user's face utilizing an inward-facing head-mounted camera comprising a sensor that supports changing of its region of interest (ROI); detecting, based on the images, a type of facial expression expressed by the user, which belongs to a group comprising first and second facial expressions; responsive to detecting that the user expresses the first facial expression, reading from the camera a first ROI that covers a first subset of facial landmarks relevant to the first facial expression; and responsive to detecting that the user expresses the second facial expression, reading from the camera a second ROI that covers a second subset of facial landmarks relevant to the second facial expression; wherein the first and second ROIs are different.

In one embodiment, the method optionally includes the following steps: calculating first relevance scores for facial landmarks extracted from a first subset of the images, selecting a first proper subset of the facial landmarks whose relevance scores reach a first threshold, and setting the first ROI to cover the first proper subset of the facial landmarks.

In one embodiment, the sensor further supports at least two different binning values for at least two different ROIs, respectively, and the method optionally includes the following steps: (i) selecting, based on performance metrics of facial expression analysis for detecting the type of facial expression expressed by the user, first and second resolutions for the first and second ROIs, respectively, and (ii) setting different binning values for the first and second ROIs according to the first and second resolutions.

Yet another aspect of this disclosure involves a non-transitory computer readable medium storing one or more computer programs configured to cause a processor-based system to execute steps of one or more embodiments of the aforementioned method.

BRIEF DESCRIPTION OF THE DRAWINGS

The embodiments are herein described by way of example only, with reference to the following drawings.

DETAILED DESCRIPTION

Figure 1:
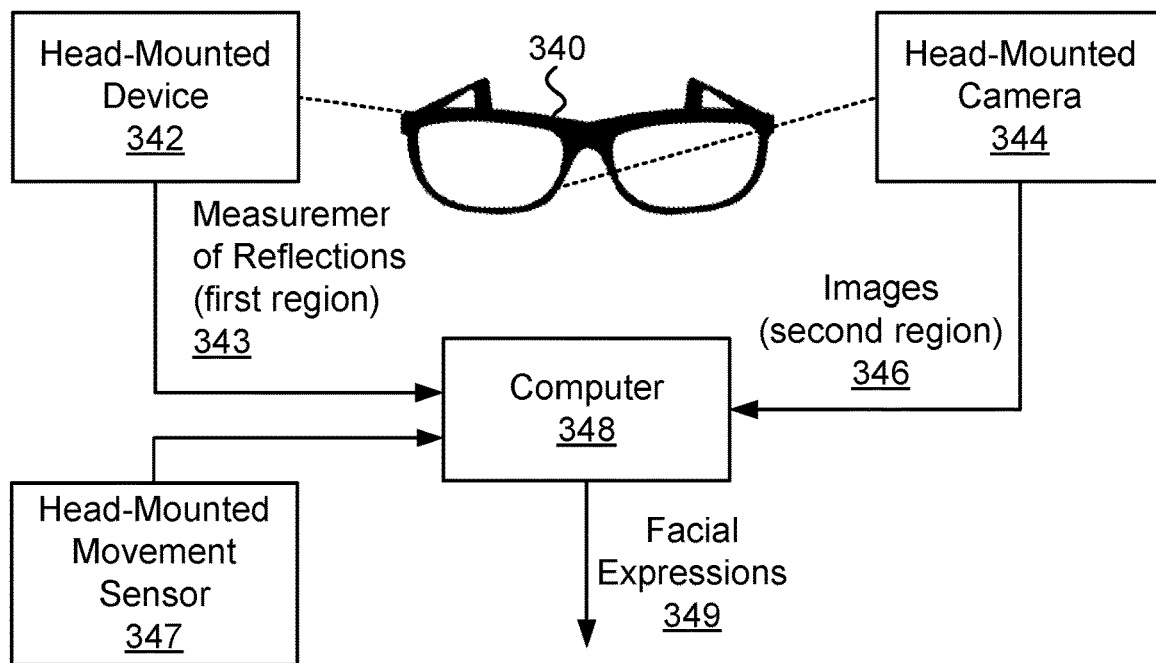
FIG. 1 illustrates an embodiment of a system that detects facial expressions using discrete photosensors and a camera.

The term "discrete photosensors" refers to very-low resolution light detectors that are relatively low cost and low power, such as photosensitive sensors, photodetectors, photodiodes, Light Emitting Diodes (LEDs) having a bi-directional characteristic with the ability to emit the light and to measure reflections, single detectors, split detectors, four-quadrant detectors, position-sensitive detectors, photo reflective sensors (for modules combining both the emitter and receiver), sensors with less than a thousand sensing pixels on the same substrate (i.e., the term discrete photosensor is not limited to a single-pixel photosensor), and arrays with direct wire connections to each pixel supporting parallel readout. The definition of discrete photosensors explicitly excludes camera sensors having thousands/millions of pixels that are equipped with suitable optics for so many pixels, such as CCD and CMOS video camera sensors having thousands/millions of pixels.

References herein to values being calculated "based on reflections" should be interpreted as the values being calculated based on measurements of the reflections (where, for example, the measurements may be measured using photosensors).

Measurements of the reflections may be expressed using various units, in different embodiments. In some embodiments, the measurements of the reflections may be the raw output of the photosensors expressed as values of voltage or illuminance (e.g., expressed as lux). In some embodiments, the measurements of the reflections may undergo various preprocessing and/or filtering using techniques known in the art.

Various embodiments described herein involve calculations based on machine learning approaches.

Herein, the terms "machine learning approach" and/or "machine learning-based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems. Herein, a "machine learning-based model" is a model trained using one or more machine learning approaches.

Herein, "feature values" (also known as feature vector, feature data, numerical features, and inputs) may be considered input to a computer that utilizes a model to perform the calculation of a value (e.g., an output, "target value", or label) based on the input. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: contextual information, information about the user being, measurements of the environment, and values of physiological signals of the user obtained by other sensors.

Sentences in the form of "inward-facing head-mounted camera" refer to a camera configured to be worn on a user's head and to remain pointed at the region it captures (some-times referred to as ROI), which is on the user's face, also when the user's head makes angular and lateral movements. A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head.

The term "smartglasses" refers to any type of a device that resembles eyeglasses, which includes a frame configured to be worn on a user's head and electronics to operate one or more sensors.

The term "visible-light camera", or simply "camera", refers to a non-contact device designed to detect at least some of the visible spectrum, such as a video camera with optical lenses and CMOS or CCD sensor; visible-light camera may be sensitive to near-infrared (NIR) wavelengths below 1050 nanometer.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, or a cooled infrared sensor). Some examples of temperature sensors useful to measure skin temperature include: thermistors, thermocouples, thermoelectric effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a magnetometer. The movement sensor may also include a sensor that measures barometric pressure.

The term "acoustic sensor" refers to a device that converts sound waves into an electrical signal. The acoustic sensor may be a microphone, such as a dynamic microphone, a piezoelectric microphone, a fiber-optic microphone, a Micro-Electrical-Mechanical System (MEMS) microphone, and/or other known sensors that measure sound waves.

The use of head-mounted devices for detecting facial expressions by emitting light from multiple light sources towards a region on the user's face, and measuring the reflections of the light from the region utilizing discrete photosensors (i.e., very-low resolution photosensors), is known in the art. The following are examples of systems and/or approaches that are known in the art and are relevant to embodiments discussed herein.

(i) The reference Masai, Katsutoshi, et al. "Evaluation of facial expression recognition by a smart eyewear for facial direction changes, repeatability, and positional drift", ACM Transactions on Interactive Intelligent Systems (TiiS) 7.4 (2017): 1-23, which is incorporated herein by reference, discloses a smart eyewear that recognizes the wearer's facial expressions in daily scenarios utilizing head-mounted photo-reflective sensors and machine learning to recognize the wearer's facial expressions.

(ii) The reference Suzuki, Katsuhiro, et al. "Recognition and mapping of facial expressions to avatar by embedded photo reflective sensors in head mounted display", 2017 IEEE Virtual Reality (VR), IEEE, 2017, (referred to herein as "Suzuki 2017"), which is incorporated herein by reference, discloses mapping of facial expressions between virtual avatars and head-mounted display (HMD) users, using retro-reflective photoelectric sensors located inside the HMD to measure distances between the sensors and the user's face.

(iii) The reference Nakamura, Fumihiko, et al. "Automatic Labeling of Training Data by Vowel Recognition for Mouth Shape Recognition with Optical Sensors Embedded in Head-Mounted Display", ICAT-EGVE, 2019, discloses utilizing photo reflective sensors and position sensitive detectors to detect facial expressions. The Photo reflective sensors, which detect the intensity of reflected light at distances between ~1 mm and 20 mm in this reference, are used to measure the upper lip and the upper cheek. And the position sensitive detectors, which detect the position from which the reflected light is received from distances of between ~10 mm and 200 mm in this reference, are used to measure the lower lip and the cheek.

(iv) The reference Yamashita, Koki, et al. "CheekInput: turning your cheek into an input surface by embedded optical sensors on a head-mounted display", Proceedings of the 23rd ACM Symposium on Virtual Reality Software and Technology, 2017, describes sensing touch gestures by detecting skin deformation using head-mounted photo-reflective sensors attached onto the bottom front of an eyewear frame to measure distances between the frame and the cheeks.

Some embodiments described herein provide improvements to efficiency and/or accuracy of detection of facial expressions based on measurements of reflections of light using discrete photosensors. FIG. 1 illustrates an embodiment of a system that detects facial expressions. The system includes a head-mounted device 342, a head-mounted camera 344, and a computer 348. Optionally, the head-mounted device 342 and/or the head-mounted camera 344 are coupled to a frame of smartglasses 340, which are configured to be worn on a user's head.

The head-mounted device 342 includes one or more light sources and discrete photosensors. The light sources emit light towards a first region on the user's face. The discrete photosensors, which are spread over more than 2 cm, take measurements 343 of reflections of the light from the first region. Herein, having discrete photosensors "spread over more than 2 cm" means that there are at least first and second discrete photosensors, from among the discrete photosensors belong to the head-mounted device 342, which are more than 2 cm apart.

It is noted that herein, the "region" in sentences in the form of "a head-mounted device . . . configured to take measurements of reflections of the light from a first region" refer to one or more regions that may or may not overlap. For example, in a specific embodiment where the device includes a first set of LEDs and photosensors pointed at the eyebrow, and a second set of LEDs and photosensors pointed at the cheek, then the first region includes a first set of possibly overlapping regions on the eyebrow and a second set of possibly overlapping regions on the cheek, with all of them being referred to as "the first region".

In one example, the head-mounted device 342 includes at least two light sources configured to emit the light, and at least three discrete photosensors configured to measure the reflections. In another example, the head-mounted device 342 includes at least two Light Emitting Diodes (LEDs) having a bi-directional characteristic with the ability to emit the light and to measure the reflections. Optionally, each of the at least two LEDs is sensitive to wavelengths equal to or shorter than the predominant wavelength it emits. Optionally, each of the at least two LEDs provides illumination when a forward voltage is applied to its electrical terminals, and acts as photodetector/photodiode for example by the following three steps: (i) apply a reverse voltage pulse for a short duration, (ii) discharge the LED's capacitance immediately afterwards, and (iii) measure the voltage across the LED to determine how much discharge of capacitance took place after a certain time. This technique is well known in the art and is further explained in publications such as (A) Akşit, Kaan, Jan Kautz, and David Luebke "Gaze-Sensing LEDs for Head Mounted Displays" arXiv preprint arXiv: 2003.08499 (2020), and (B) Dietz, Paul, William Yerazunis, and Darren Leigh "Very low-cost sensing and communication using bidirectional LEDs" International Conference on Ubiquitous Computing, Springer, Berlin, Heidelberg, 2003.

The head-mounted camera 344 captures images 346 of a second region on the face. Optionally, the images 346 are captured at a rate that is lower than a rate at which the measurements 343 are taken. In one example, an average rate at which the measurements 343 are taken is at least ten times an average rate at which the images 346 are captured.

In some embodiments, the head-mounted camera 344 utilizes a sensor that has more than 100 pixels. In these embodiments, the head-mounted camera 344 may have a lens, and the sensor plane of the head-mounted camera 344 may be tilted by more than 2° relative to the lens plane of the head-mounted camera 344, according to the Scheimpflug principle in order to capture sharper images.

In one embodiment, the first region includes a portion of the user's nose, and both the head-mounted device 342 and the head-mounted camera 344 are mounted below the user's eye level.

In another embodiment, the first region includes a portion of a cheek of the user, and the head-mounted device 342 is mounted below the user's eye level.

In one embodiment, the head-mounted device 342 and the head-mounted camera 344 are fixed to the frame of the smartglasses 340. Optionally, at least a portion of the first region is located less than 4 cm from one of the user's eyeballs, the second region is located in a known position relative to the first region, and the first and second regions overlap. Alternatively, at least a portion of the first region is located less than 2 cm from one of the user's eyeballs, the second region is located in a known position relative to the first region, and the first and second regions do not overlap and have a minimal distance between their borders below 2 cm.

Herein, determining the distance of a region from the eyeballs is based on estimations of the distances and locations of facial landmarks detectable by the head-mounted device 342 when a typical (average) user who wears the smartglasses. Similarly, determining the relative location of the first and second regions is done based on the estimated location of the first and second regions on the face of a typical user wearing the smartglasses. Additionally or alternatively, determining the distance of a region from the eyeballs and/or determining the relative location of the first and second regions may be done based on images of the user's face taken with the head-mounted camera 344 or an additional, non-head-mounted camera.

Figure 2A:
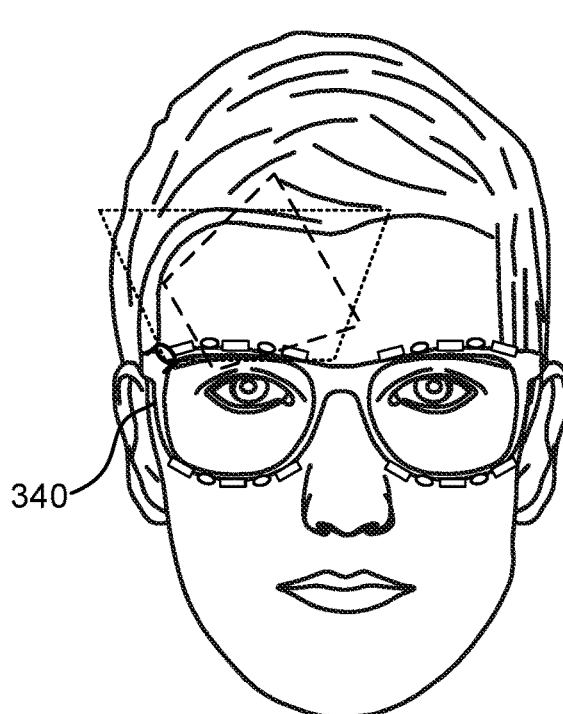
FIG. 2A illustrates an embodiment of smartglasses to which are couple a head-mounted device and a head-mounted camera, which are used to detect facial expressions.
Figure 2B:
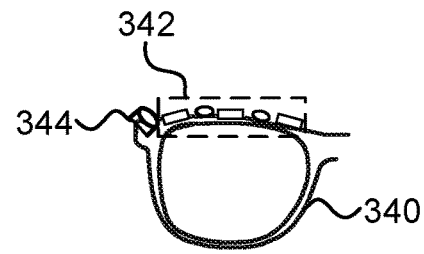
FIG. 2B illustrates a closeup view in which a portion of the smartglasses is depicted.
Figure 2C:
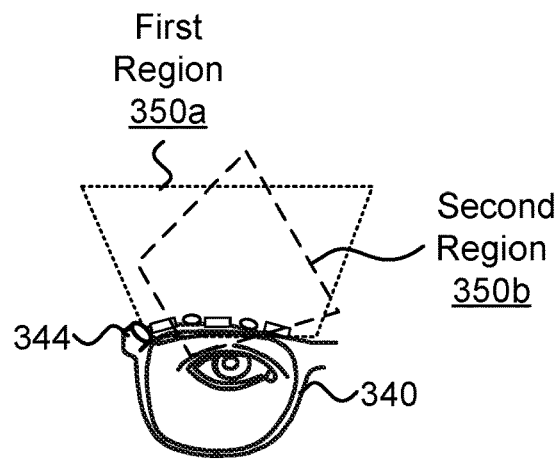
FIG. 2C illustrates a closeup of the same portion of the smartglasses depicted in FIG. 2B, with a detailed illustration of different measured regions.

FIG. 2A illustrates an embodiment of smartglasses 340 to which the head-mounted device 342 and the head-mounted camera 344 are coupled. FIG. 2B illustrates a closeup view in which a portion of the smartglasses 340 are depicted. In this figure, the head-mounted device 342 includes three discrete photosensors (rectangle shaped) and two emitters (oval shaped). FIG. 2C is a closeup of the same portion of the smartglasses 340 depicted in FIG. 2B, with a detailed illustration of a first region 350a and a second region 350b. The first region 350a, which is detectable from light that is emitted from the emitters of the head-mounted device 342 and whose reflections are measured using the discrete photosensors of the head-mounted device 342. The second region 350b appears in images captured by the head-mounted camera 344. Note that in this example, the first region 350a and the second region 350b overlap to some extent. In other examples, the first and second regions may be disjoint, or one of the regions may be entirely included in the other region.

The computer 348 calculates, based on the images 346, one or more extents of respective one or more interferences. Optionally, each of the one or more interferences may affect the measurements 343. For example, an interference may increase or decrease intensity of measured reflections. Extents of various types of interferences may be determined based on the images 346. Optionally, these values include indications of changes to color of regions in the images 346, compared to previously taken baseline images depicting those regions. Optionally, to calculate the extent of an interference, the computer 348 analyzes one or more of the images 346 using imaging processing techniques, as discussed below.

Figure 13A:
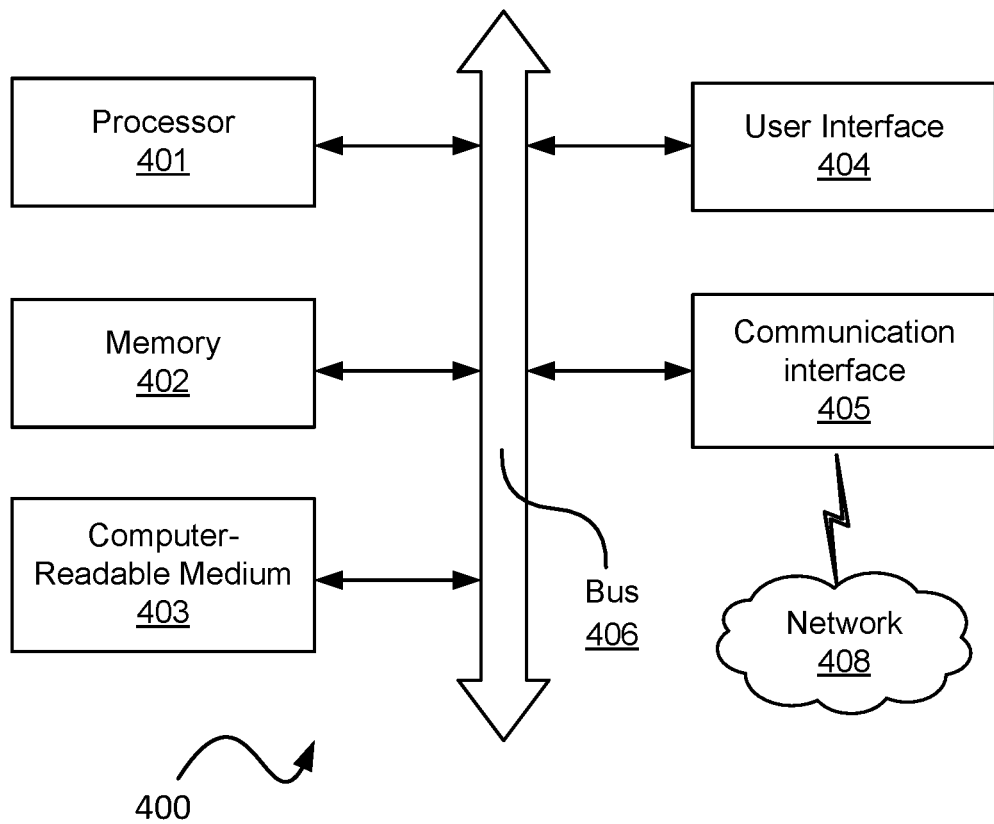
FIG. 13A and FIG. 13B are schematic illustrations of possible embodiments for computers.
Figure 13B:
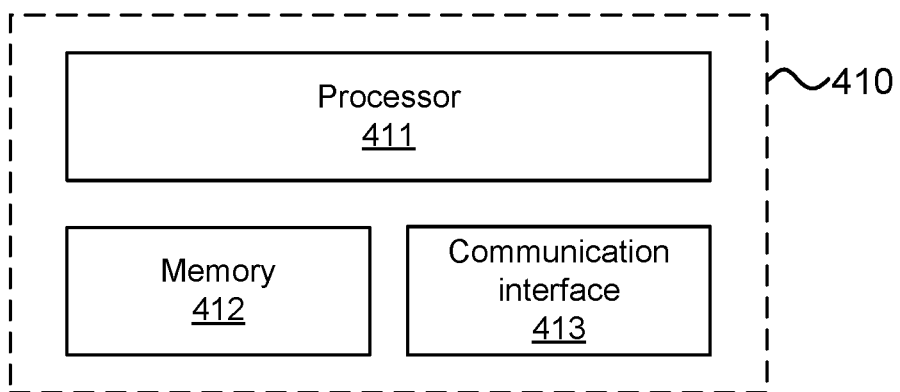

Examples of computers that may be utilized in embodiments described herein, such as the computer 348, computer 358, computer 518, computer 534, and computer 546, are computers modeled according to computer 400 or computer 410 illustrated in FIG. 13A and FIG. 13B, respectively. It is to be noted that the use of the singular term "computer" is intended to imply one or more computers, which jointly perform the functions attributed to "the computer" herein. In particular, in some embodiments, some functions attributed to a "computer" (e.g., one of the aforementioned computers) may be performed by a processor on a wearable device (e.g., smartglasses) and/or a computing device of the user (e.g., smartphone), while other functions may be performed on a remote processor, such as a cloud-based server.

Figure 3:
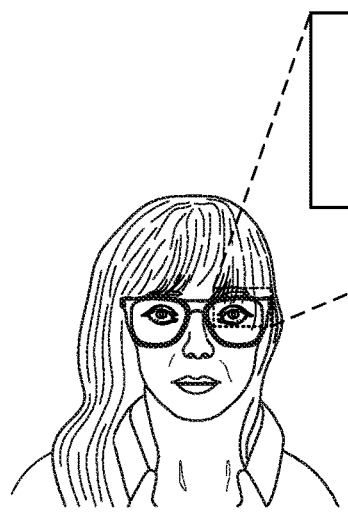
FIG. 3 illustrates a scenario in which hair falls on the eyebrow.

Hair that covers a portion of the first region, and/or hair that moves over a portion of the first region, may change the colors and topography of the surface that reflects the light measured by the discrete photosensors, and thus, affect the detection of the facial expressions based on measurements of the reflections. In a first example of calculation of an extent of an interference, the computer 348 calculates an extent of presence of hair over a first portion of the first region. FIG. 3 illustrates a scenario in which hair falls on the eyebrow. Such a scenario could interfere with measurements of reflections by the head-mounted device 342 illustrated in FIG. 2A to FIG. 2C. Some embodiments described herein can detect the presence of hair and account for it in order to improve detections of facial expressions, as discussed below.

Application of makeup to the face may change the colors and topography of the surface that reflects the light measured by the discrete photosensors, and thus affect the detection of the facial expressions based on the measurements of the reflections. In a second example, the computer 348 calculates, based on the images 346, a certain value indicative of an extent of makeup applied over a second portion of the first region. Optionally, to calculate the extent, the computer 348 analyzes one or more of the images 346 using imaging processing techniques, as discussed below, to obtain characteristics of the makeup application. Examples of characteristics of the makeup include values indicative of the effect of the makeup on the reflections, and an index representing different makeup material and/or shades applied on the face.

Figure 4:
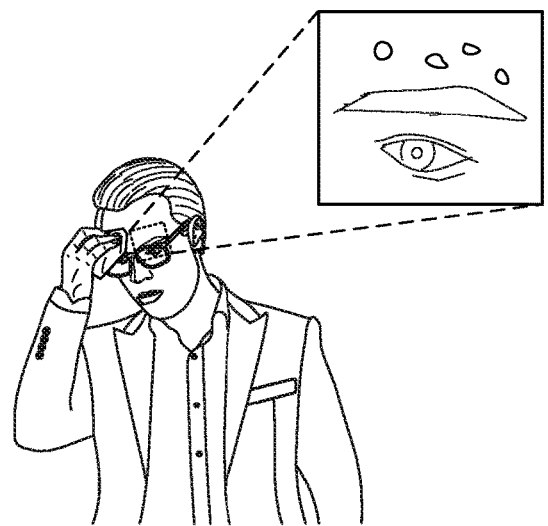
FIG. 4 illustrates a scenario in which there is perspiration above the eyebrow.

Events such as perspiration, getting wet in the rain, a change in the environment humidity level, and/or direct wind hitting the user's face, may cause a change in the level of skin wetness, which can affect the colors and topography of the surface that reflects the light measured by the discrete photosensors, and thus affect the detection of the facial expressions based on the measurements of the reflections. In third example, the computer 348 calculates, based on the images 346, a change in a level of skin wetness at a third portion of the first region. FIG. 4 illustrates a scenario in which there is perspiration above the eyebrow. Such a scenario could interfere with measurements of reflections by the head-mounted device 342 illustrated in FIG. 2A to FIG. 2C. Some embodiments described herein can detect the presence of perspiration and account for it in order to improve detections of facial expressions, as discussed below.

Skin infections, such as acne, may change the colors and topography of the surface that reflects the light measured by the discrete photosensors, and thus affect the detection of the facial expressions based on the measurements of the reflections. In a fourth example, the computer 348 calculates, based on the images 346, an extent of skin infection at a fourth portion of the first region.

In some examples, at least some of the portions of the first region, from among the aforementioned first, second, third, and fourth portions, may overlap with each other (and even cover the same area of the first region). In other examples, at least some of the portions of the first region, from among the aforementioned first, second, third, and fourth portions, do not overlap.

The computer 348 utilizes data that includes the measurements 343 and the images 346 in order to detect facial expressions of the user. In one example, detection of facial expressions involves selecting what type of facial expression is being expressed by the user at different times. For example, at different points of time, the computer 348 may determine which facial expression is being expressed from among a predetermined set of facial expressions, such as happiness, disgust, anger, surprise, fear, sadness, or a neutral facial expression. In another example, detection of facial expressions involves calculating probabilities that a facial expression that is being expressed at a certain time corresponds to each emotion from among a predetermined set of different emotions.

As mentioned above, detection of facial expressions based on measurements of reflections of the light from regions of the face utilizing head-mounted discrete photosensors is known in the art. Some embodiments described herein improve this detection process by identifying and/or accounting for interreferences (hair, makeup, etc.) that may affect the measurements and lead to less accurate detections of facial expressions.

In some embodiments, an average rate at which the measurements 343 are taken is at least 50 times higher than an average rate at which the images 346 are captured, and the average rate at which the facial expressions are detected is at least 10 times higher than the average rate at which the images 346 are captured. In one example, the measurements 343 are measured at an average rate of 50 Hz, the computer 348 processes the measurements 343 and detects the facial expressions at an average rate of 25 Hz, based on the measurements 343 of the reflections, the images 346 are captured at an average rate of 0.5 Hz, and the computer 348 utilizes the images 346 for calibrations at an average rate of 0.5 Hz for calculations involved in detecting the facial expressions based on the measurements 343. Optionally, the calibration involves calculating values indicative of the extent of an interference and/or the effect of an interference (e.g., based on an identified extent of interference), as discussed below.

Calculating the extent of an inference based on the images 346 may be done in different ways. Optionally, to calculate the extent of the interference, the computer 348 may utilize image analysis approaches known in the art, and utilize these approaches to calculate one or more values indicative of an extent of an interference that may influence measurements of reflections from the first region, such as hair, makeup, skin wetness, and/or a skin infection. Some of object detection methods known in the art that may be utilized (e.g., to detect hair, makeup, skin wetness, and/or infection) are surveyed in Zou, Zhengxia, et al. "Object detection in 20 years: A survey." arXiv preprint arXiv:1905.05055 (2019).

In some embodiments, the computer 348 utilizes a machine learning-based approach to detect an extent of an interference based on the images 346. In these embodiments, the computer 348 generates image-based feature values from one or more of the images 346, and utilizes a model (referred to herein as an "interference detection model") to calculate, based on the image-based feature values, a value indicative of an extent of an interference. This value may be utilized by the computer 348, as discussed below, to detect a facial expression.

Various image-based feature values may be generated by the computer 348 from the images 346. In one embodiment, at least some of the image-based feature values may be derived directly from values of pixels in images 346. Optionally, at least some of the image-based feature values are values of pixels from the images 346 or some simple function of the pixels in the images 346, such as the average of pixels at certain regions in each of the images. Optionally, one or more of the image-based feature values may be various low-level features derived from images 346, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the image-based feature values may be derived from multiple images taken at different times, such as volume local binary patterns (VLBP), cuboids, and/or optical strain-based features.

In one not limiting example, the feature values generated from the images 346 include products of Gabor filters.

In some embodiments, at least some of the feature values described above are generated for previously taken images of the second region (baseline images) with the head-mounted camera 344.

In addition to image-based feature values in some embodiments, calculation of the extent of an interference using the interference detection model may involve utilization of other feature values generated based on additional measurements taken at times corresponding to when the images 346 were captured. In one example, the additional measurements include the measurements 343. In another example, the additional measurements include measurements of the environment (e.g., temperature, humidity, etc.) representing the condition of the environment at the time the images 346 were captured.

In some embodiments, an interference detection model that is utilized to calculate the extent of a certain type of interference (e.g., hair on a portion of the first region) is generated by collecting labeled training samples. Optionally, each of the labeled training samples include feature values generated based on images taken with the head-mounted camera 344 and label indicative of the extent of the interference (e.g., the proportion of the first region that is covered by hair). In one example, a label may be generated manually (e.g., by a human labeler viewing the image). In another example, the label may be generated based on analysis of additional images taken at a different angle (e.g., a front-facing non-head-mounted camera). Optionally, the training samples includes one or more samples generated based on images of the user.

It is to be noted that in some embodiments the first region (measured with the head-mounted device 342) may include areas that are not part of the second region (which is captured in the images 346). Thus the whole interference (e.g., hair on a portion of the first region) may not be depicted in the images (which are of the second region), but may be detectable in an additional source of data used to generate labels (e.g., a non-head-mounted camera).

The training samples may then be provided to a machine learning training algorithm that trains the interference detection model based on the training samples. For example, the training algorithm may be a regression algorithm or an algorithm for training neural networks (e.g., a deep learning neural network). Once the interference detection model is trained, it may be utilized to detect interferences in unlabeled samples, such as samples that include feature values generated from the images 346.

In one non-limiting example, the computer 348 utilizes a convolutional neural network (CNN) trained on the aforementioned training samples, using approaches known in the art, in order to detect an extent of an interference.

Depending on the embodiment, the phrase an "extent of an interference" may refer to different types of values. In some examples, an extent of an interference may be a binary value indicating whether or not the interference reaches a threshold. For example, the value may indicate whether or not there is hair detected at the first region, or whether the portion of the first region in which hair is detected is at least a certain size. In other examples the extent of the interference may be a numerical value indicating a property such as the proportion of the first region in which the interference occurs (e.g., the proportion of the first region on which hair is detected).

Similarly, with other types of interferences, the extent may be indicative of whether or not the level of skin wetness (e.g., due to perspiration) reaches a threshold, whether or not there is makeup applied, and whether a skin infection is detected. Additionally or alternatively, and extent of an interference may be indicative of the size of the area (i.e., what portion of the first region) exhibits the property associated with the interference (e.g., makeup, wetness, or a skin infection).

In some embodiments, the extent of an interference is a value calculated based on comparison of the images 346 with baseline images, taken with the head-mounted camera 344, when the interference was not present. For example, the extent of makeup and/or a skin infection may be determined by comparing detected skin tone in the images 346 with the skin tone of the user determined from previous images taken with the head-mounted camera 344.

In some embodiments, the computer 348 utilizes the images 346 to calculate an effect of the extent of the interference on the measurements 343 of the reflections. For example, the effect may be one or more values that indicate an change in the intensity of the measured reflections due to the presence of the interference (compared to intensities that would be expected to be measured had no interference been present). Optionally, the one or more values quantify the change in intensity of the measured reflections. Optionally, the effect of an interference on measurements of reflections is calculated on a regional basis. For example, the one or more values may include multiple values describing the effect of the interference on values measured by different discrete photosensors from among the discrete photosensors belonging to the head-mounted device 342. In another example, the one or more values may include multiple values describing effects of interferences at different portions of the first region on values measured by different discrete photosensors from among the discrete photosensors belonging to the head-mounted device 342.

The effect of an interference (such as presence of hair, makeup, and/or perspiration) on the measurements of the reflections may be calculated in various ways, such as using a precompiled table and/or a machine learning-based approach.

In one embodiment, calculating the effect of having a certain extent of an interference (e.g., detecting hair on a portion of the first region) is done utilizing a table that has precomputed values that quantify the effect. Optionally, the precomputed values are calculated based on comparing intensities of previous measurements of reflections, from the user's face, measured by the head-mounted device 342 at different times. The previous measurements include a first set measurements of reflections taken when there was no interference detected at the first region (e.g., no hair detected), and a second set of measurements of reflections taken when there was an interference detected at the first region (e.g., hair was detected over a portion of the first region). Thus, differences between the first and second sets correspond to values of the effect of the interference. In this embodiment, the first set of measurements can serve as a baseline to which different extents of interferences may be compared, and thus the effects of the different extents can be quantified and used as values in a lookup table that provides the effect of an interference (on values of measurements of reflections) according to its calculated extent (based on images). This approach may be extended to involve multiple sets of measurements with different extents of interferences or different ranges of extents of interferences.

In one example, data used to calculate the aforementioned table of values quantifying the effect of an interference is collected at different times, on different days, and/or in different environmental conditions (e.g., lighting conditions, indoor vs. outdoors, etc.) Collecting such a diverse training set of data can assist in compiling a more robust table. In another example, data is collected while the user exhibits a specific facial expression (e.g., a neutral facial expression), which may be detected based on images captured by the head-mounted camera 344 or by measurements from some other sensors (which may be head-mounted or non-head-mounted). Having data collected with consistent facial expressions can assist in obtaining a more robust quantification of the effect of an interference (by minimizing the effect on the reflections due to variations of the facial expression).

In one embodiment, calculating the effect of having a certain extent of an interference (e.g., detecting hair on a portion of the first region) is done utilizing a machine learning-based approach. The computer 348 calculates feature values based on images captured by the head-mounted camera 344 (and optionally additional data, as described below). The computer 348 utilizes a model (referred to herein as an "effect model") to calculate, based on the feature values, one or more values indicative of the effect of an interference (which is represented in the images from which feature values were calculated). Optionally, the effect model is generated based on samples that are generated from training data that includes previously taken images (captured by the head-mounted camera 344). Optionally, the training data also includes previous measurements of reflections measured by the head-mounted device 342 at the times the previously taken images were captured. Optionally, the training data also includes additional data such as values of environmental conditions and/or identification of facial expressions that were expressed while the previously taken images were captured. Optionally, each training sample includes feature values generated based one or more of the aforementioned training data types and a label, as explained below.

One or more of the feature values generated based on images captured by the head-mounted camera 344 may be image-based feature values discussed above. In one example, the one or more feature values include values describing the brightness and/or color of certain pixels and/or portions of the first region. In another example, one or more feature values are indicative of the extent of the interference (e.g., a value obtained using an approach described above for calculating the extent of an interference).

In some embodiments, the feature values used to calculate the one or more values indicative of the effect of an interference are indicative of environmental conditions (e.g., brightness of the environment, temperature of the environment, etc.) and/or values indicative of the type of facial expression being expressed (e.g., as determined based in images captured by the head-mounted camera 344 and/or measurements of reflections by the head-mounted device 342).

In one embodiment, labels of training samples used to train the effect model are indicative of the effect of an interference on the measurements of the reflections. Optionally, the effect is determined by comparing first and second measurements of reflections taken at first and second times. The first and second times are selected based on images captured by the head-mounted camera 344, such that they represent similar conditions with the exception of the interference. For example, the first and second times involve the face being in similar environmental conditions (e.g., direction and intensity of the natural lighting) and/or when the user expressed a similar facial expression, but at the first time there was no hair covering the first region and at the second time there was hair covering a portion of the first region.

Values of extents of interferences and/or effects of interferences are utilized in embodiments described herein in the process of detection of facial expressions from measurements of reflections (the measurements 343). In one embodiment, the computer 348 utilizes a machine learning-based approach to detect the facial expressions, in which the computer 348 generates feature values based on the measurements 343 and the images 346, and utilizes a model (referred to herein as a "facial expression detection model") to calculate, based on the feature values, a value indicative of whether the user expressed a certain facial expression. Optionally, the facial expression detection model is generated based on data that includes previously taken measurements of the user (taken with the head-mounted device 342) and previously captured images of the user (captured with the head-mounted camera 344), as discussed below.

There are various machine learning-based approaches known in the art for detecting facial expressions from measurements of discrete photosensors. Some embodiments described herein involve inclusion of indications of the extent of and interference (e.g., hair or makeup) and/or an effect in order to make detections of facial expressions more accurate. Optionally, this involves generation of at least some feature values used for the detection of the facial expressions based on the measurements 343 using one or more known approaches. In addition, one or more of the feature values used for the detection of the facial expressions are generated based on the images 346 (and optionally other inputs such as the measurements 343), and theses one or more feature values provide an indication of an extent of an interference and/or an effect of the interference.

In one embodiment, the computer 348 generates at least some feature values from the measurements 343 using the values of the measured reflections as features after normalization according to a technique described in Masai, Katsutoshi, et al. "Evaluation of facial expression recognition by a smart eyewear for facial direction changes, repeatability, and positional drift". In another embodiment, the computer 348 generates at least some feature values from the measurements 343 using the values of the measured reflections as features after normalization according to a technique described in Suzuki 2017.

In addition to feature values describing intensities of measured reflections, the computer 348 may calculate one or more values, based on the images 346, which are indicative of an extent of a certain interference and/or the effect of the certain interference (on the measurements 343), and utilize the one or more values in the detection of the facial expressions. For example, the computer 348 may generate one or more features values, based on the images 346, that correspond to values of extents of interferences and/or effects of the interferences, and utilize these one or more feature values along with feature values generated from the measurements 343 in order to detect facial expressions.

In a first example, the computer 348 calculates, based on the images 346, a first value indicative of an extent of hair on a first portion of the first region and/or indicative of an effect of the presence of the hair on the first portion of the first region, and utilizes the first value in the detection of the facial expressions. Optionally, at least one of the feature values is generated based on the first value.

In a second example, the computer 348 calculates, based on the images 346, a second value indicative of an extent of makeup applied over a second portion of the first region and/or indicative of an effect of the presence of the makeup applied over the second portion of the first region, and utilizes the second value in the detection of the facial expressions. Optionally, at least one of the feature values is generated based on the second value.

In a third example, the computer 348 calculates, based on the images 346, a third value indicative of a change in a level of skin wetness at a third portion of the first region and/or indicative of an effect of the change in the level of skin wetness at the third portion of the first region, and utilizes the third value in the detection of the facial expressions. Optionally, at least one of the feature values is generated based on the third value.

In a fourth example, the computer 348 calculates, based on the images 346, a fourth value indicative of an extent of skin infection at a fourth portion of the first region and/or indicative of an effect of the skin infection at the fourth portion of the first region, and utilizes the fourth value in the detection of the facial expressions. Optionally, at least one of the feature values is generated based on the fourth value.

In some embodiments, feature values generated by the computer 348, which are used for facial expression detection, may account for multiple interferences. These feature values may include values indicative of the extent of various interferences involving different areas on the face (e.g., different portions of the first region) and/or the effect of various interferences at different areas. In is noted that the relationship between the different areas may vary between embodiments, so in some examples, these areas may coincide and/or overlap, while in other examples they do not overlap.

In one example, the computer 348 generates feature values that include a first feature value calculated based on the images 346, which is indicative of an effect on the measurements 343 due to the presence of the hair over the portion of the first region, and a second feature value calculated based on the images 346, which is indicative of the additional effect on the measurements 343 of due to the makeup applied over the additional portion of the first region.

In another example, the computer 348 generates feature values that include a first feature value, calculated based on the images 346, which is indicative of an effect on the measurements 343 due to the presence of the hair over the portion of the first region, and a second feature value, calculated based on the images 346, which is indicative of the additional effect on the measurements 343 due to the change in a level of skin wetness at the additional portion of the first region.

In yet another example, the computer 348 generates feature values that include a first feature value, calculated based on the images 346, which is indicative of an effect on the measurements 343 due to the presence of the hair over the portion of the first region, and a second feature value, calculated based on the images 346, which is indicative of an additional effect on the measurements 343 due to the skin infection at the additional portion of the first region.

Feature values described above (corresponding to intensities of measured reflections and to the extent and/or effect of one or more interferences) are provided as input used to detect facial expressions. In some embodiments, the computer 348 utilizes the facial detection model to calculate, based on these feature values, a value indicative of a facial expression being expressed by the user at the time. Training the facial expression detection model involves collecting training samples that include feature values generated from previously taken measurements of the user (taken with the head-mounted device 342) and previously captured images of the user (captured with the head-mounted camera 344). Additionally, the training samples include labels describing the facial expressions expressed at the time these images were taken. Optionally, these labels may be determined based on analysis of images of the face captured using non-head-mounted cameras, using techniques known in the art, such as approaches discussed in Y.-1. Tian, et al. "Recognizing action units for facial expression analysis", *IEEE Trans. Pattern Anal. Mach. Intell.*, 23(2):97-115, February 2001.

The training data describe above can be provided to a machine learning training algorithm in order to generate the facial expression detection model. In one example, the training data is utilized to train a support vector machine (SVM) with a radial basis function (rbf) kernel algorithm as described in Masai, Katsutoshi, et al. "Evaluation of facial expression recognition by a smart eyewear for facial direction changes, repeatability, and positional drift". In another example, the training data is utilized to train a neural network classifier, as described in Suzuki 2017.

It is to be noted that in some embodiments, additional head-mounted devices may be utilized to take measurements of reflected lights from additional regions on the user's face. Similarly, additional head-mounted cameras may be utilized to capture images from which extents of interferences at the additional regions may be determined. In a similar fashion to the discussed above, feature values can be generated from these additional measurements and images and be utilized to detect facial expressions. In one example, the facial expressions are detected utilizing measurements from first and second head-mounted devices that measure regions on the right and left sides of the face, respectively, and images captured by first and second head-mounted cameras capturing images of additional regions on the right and left sides of the face, respectively.

Different facial expressions may deform different parts of the face to different extents, thus, the relevancy of different light sources during different facial expressions, may not be the same. In order to save power, the system may operate more relevant light sources of the discrete photosensors belonging to the head-mounted device 342 for a specific facial expression more frequently than less relevant light sources for the specific facial expression. In one embodiment, the computer 348 operates the light sources according to first and second different schedules responsive to detecting first and second different facial expressions belonging to the facial expressions, being detected. For example, the computer 348 may operate certain light sources at least twice more frequently and/or at at least twice the brightness according to the first schedule compared to the frequency and/or brightness at which they are operated according to the second schedule. In one example, light sources aimed at the edges of the mouth are operated according to the first schedule when a smile is detected and according to the second schedule when an expression of surprise it detected.

The reflectance of the eyebrow is different from the skin. For example, the eyebrow may be darker than the skin and have a lower reflectance in near infrared (NIR) light than its surrounding skin. As a result, movements of the eyebrow change the measured NIR reflections. Additionally, until some extent, there is usually a relationship between interesting facial expressions and head movements; thus, in order to save power, the system may increase the rate of emitting the light when the head movements reach a threshold. In one embodiment, the first region includes a portion of an eyebrow of the user, and both the head-mounted device 342 and the head-mounted camera 344 are mounted above the user's eye level. In this embodiment, the system also includes a head-mounted movement sensor 347 that measures movements (e.g., an accelerometer). The computer 348 emits the light at a first rate when the movements are below a threshold, and emits the light at a second rate, which is higher than the first rate, when the movements are above the threshold.

In some embodiments, measurements taken by the head-mounted device 342 are used to detect when the user expresses a certain facial expression, such as a neutral facial expression, in order to collect imaging photoplethysmography (iPPG) signals during that time. This may enable better comparison of iPPG values from different times, and may also result in collecting more accurate signals (depending on the certain facial expression). Optionally, the iPPG values are calculated based on images captured by the head-mounted camera 344 while the user expressed a neutral facial expression, and the reflections are used to detect the times the user expresses the neutral facial expression.

The following method may be used by systems modeled according to FIG. 1. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting, by a head-mounted device (e.g., the head-mounted device 342), light towards a first region on a user's face, and taking, using discrete photosensors, measurements of reflections of the light from the first region.

In Step 2, capturing, by a head-mounted camera (e.g., the head-mounted camera 344), images of a second region on the face.

In Step 3, calculating, based on the images taken in Step 2, an extent of presence of hair over a portion of the first region.

And In Step 4, detecting facial expressions of the user based on the measurements of the reflections taken in Step 1 and the extent calculated in Step 3.

In some embodiments, detecting the facial expressions involves utilizing a machine learning-based approach. Optionally, this involves steps of generating feature values based on data comprising the images and measurements of the reflections, and utilizing a model for calculating, based on the feature values, values indicative of the facial expressions of the user. Optionally, at least one of the feature values calculated based on the images is indicative of the effect on the measurements of the reflections due to the presence of the hair over the portion of the first region.

In addition to the presence of hair, in some embodiments, the method involve detection of additional types of interferences. In one embodiment, the method optionally includes the following steps: (i) calculating, based on the images, a certain value indicative of an extent of makeup applied over an additional portion of the first region; and (ii) utilizing the certain value in the detection of the facial expressions in Step 4.

In one embodiment, detecting the facial expressions involves utilizing a machine learning-based approach that includes the following steps: generating feature values based on data comprising the images and measurements of the reflections, and utilizing a model for calculating, based on the feature values, values indicative of the facial expressions of the user. Optionally, the feature values comprise a first feature value calculated based on the images which is indicative of the effect on the measurements of the reflections due to the presence of the hair over the portion of the first region, and a second feature value calculated based on the images, which is indicative of the additional effect on the measurements of the reflections due to the makeup applied to the additional portion of the first region.

Figure 5:
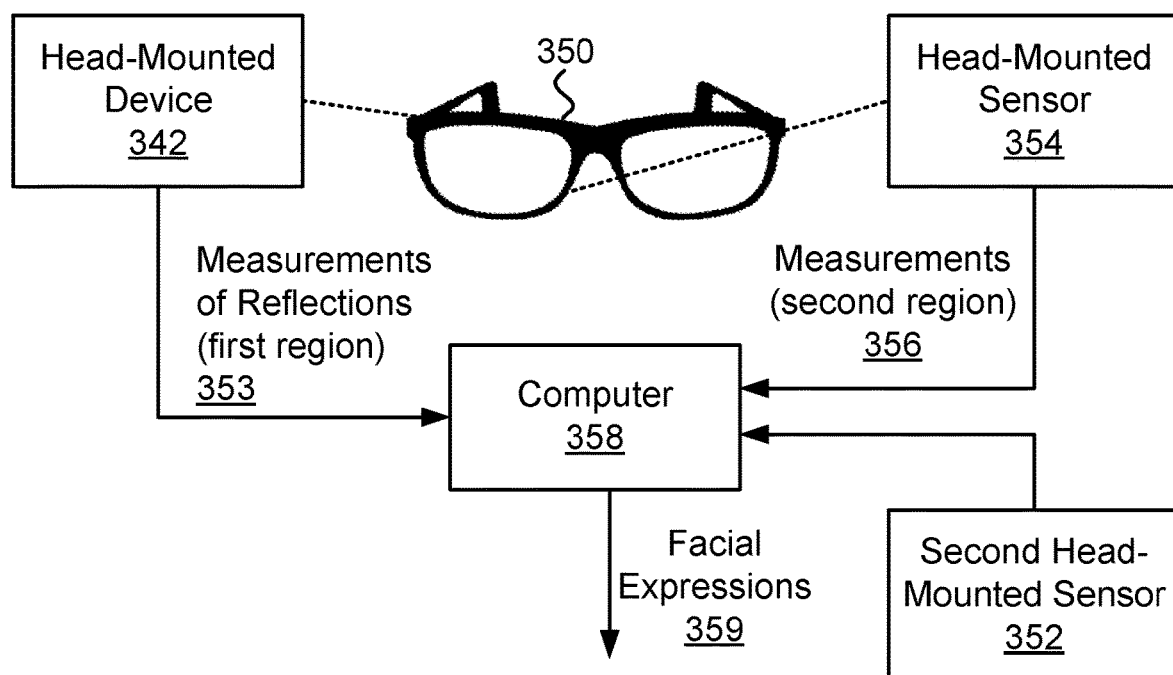
FIG. 5 illustrates an embodiment of a system that detects facial expressions, in which different types of devices may be utilized to measure an extent of skin wetness on the face.

FIG. 5 illustrates an embodiment of a system that detects facial expressions, in which different types of devices may be utilized to measure an extent of skin wetness on the face in order to make the detections of the facial expressions more accurate. In one embodiment, the system includes at least the head-mounted device 342, a head-mounted sensor 354, and a computer 358. Optionally, the system includes also a second head-mounted sensor 352. Optionally, one or more of the system's components are coupled to a frame of smartglasses 350.

In one embodiment, the head-mounted device 342 includes light sources that emit light towards a first region on a user's face, and discrete photosensors, spread over more than 2 cm, that take measurements 353 of reflections of the light from the first region (also referred to as "the measurements 353", "the first measurements 353", or "first measurements").

The head-mounted sensor 354 takes measurements 356 of a second region on the face (also referred to as "the measurements 356", "the second measurements 356", or "second measurements"). Different types of sensors may be utilized to take the second measurements 356 in different embodiments, as discussed below.

In one embodiment, the head-mounted device 342 and the head-mounted sensor 354 are fixed to the frame of the smartglasses 350. In this embodiment, at least a portion of the first region is located less than 2 cm from one of the user's eyeballs, the second region is located in a known position relative to the first region, and the first and second regions do not overlap. In another embodiment, the first region includes a portion of the user's nose, and both the head-mounted device 342 and the head-mounted sensor 354 are mounted below the user's eye level. In yet another embodiment, the first region includes a portion of a cheek of the user, and the head-mounted device is mounted below the user's eye level.

In one embodiment, the system includes the second head-mounted sensor 352 that measures temperature and/or humidity levels of the environment. Optionally, the second head-mounted sensor 352 is coupled to the frame of the smartglasses 350.

The computer 358 calculates a level of skin wetness based on the measurements 356, and detects facial expressions of the user based on the measurements 353 and the level of skin wetness. Optionally, the computer 358 refines the calculation of the level of skin wetness based on the temperature and/or humidity levels measured by the second head-mounted sensor 352. Optionally, an average rate at which the measurements 353 are taken is at least ten times higher than an average rate at which the second measurements 356 are taken.

Different types of sensors may be utilized to take the second measurements 356. In some embodiments, the head-mounted sensor 354 includes electrodes and the second measurements 356 include values indicative of level of skin conductance. In this embodiment, the computer 358 calculates the level of skin wetness based on the values indicative of the skin conductance. Optionally, an average rate at which the first measurements 353 are taken is at least ten times higher than an average rate the value indicative of the of level of skin conductance are taken. For example, on average, each discrete photosensor belonging to the head-mounted device 342 provides at least ten measurements of reflections for each value indicative of skin conductance.

In one embodiment, in which the head-mounted sensor 354 includes electrodes, the head-mounted device 342 and the head-mounted sensor 354 are fixed to the frame of the smartglasses 350. In this embodiment, the head-mounted sensor 354 and the head-mounted device 342 are positioned such that at least a portion of the first region is located less than 4 cm from one of the user's eyeballs, and the second region is located in a known position relative to the first region.

In another embodiment, in which the head-mounted sensor 354 includes a camera, the second measurements 356 include images of the second region, and the computer 358 calculates the level of skin wetness based on analyzing the images. In this embodiment, the computer 358 utilizes the images in a similar fashion to how the computer 348 utilizes images to calculate an extent of an interference that involve skin wetness, as discussed above. Optionally, in this embodiment, an average rate at which the measurements 353 are taken is at least ten times higher than an average rate at which the images are captured. In one example, the head-mounted device 342 and the head-mounted sensor 354 are fixed to the frame of the smartglasses 350, at least a portion of the first region is located less than 4 cm from one of the user's eyeballs, the second region is located in a known position relative to the first region, and the first and second regions overlap.

Similarly to the computer 348, the computer 358 utilizes data that includes the measurements 353 and the measurements 356 in order to detect facial expressions of the user. Some embodiments described herein improve this detection process by identifying and/or accounting for skin wetness that may affect the measurements 353 and lead to less accurate detections of facial expressions. In one embodiment, the computer 358 utilizes a machine learning-based approach to detect the facial expressions, in which the computer 358 generates feature values based on the measurements 353 and the measurements 356, and utilizes a model (referred to herein as a "facial expression detection model") to calculate, based on the feature values, a value indicative of whether the user expressed a certain facial expression. Optionally, the facial expression detection model is generated based on data that includes previously taken measurements of the user (taken with the head-mounted device 342) and previously taken measurements taken with the head-mounted sensor 354.

In one embodiment, the computer 358 generates at least some feature values from the measurements 353 using the values of the measured reflections as features after normalization according to a technique described in Masai, Katsutoshi, et al. "Evaluation of facial expression recognition by a smart eyewear for facial direction changes, repeatability, and positional drift". In another embodiment, the computer 358 generates at least some feature values from the measurements 353 using the values of the measured reflections as features after normalization according to a technique described in Suzuki 2017.

In addition to feature values describing intensities of measured reflections, the computer 358 may calculate one or more values, based on the measurements 356, which are indicative of a level of skin wetness (on the face) and/or the effect of the skin wetness, and utilize the one or more values in the detection of the facial expressions. For example, the computer 358 may generate one or more features values, based on the measurements 356, that correspond to values of extents of the skin wetness and/or effects of the skin wetness (e.g., on values of measured reflections), and utilize these one or more feature values along with feature values generated from the measurements 353 in order to detect facial expressions.

Calculating the level of skin wetness based on the second measurements 356 may be done in different ways. In one embodiment, a precomputed table indicates, for different values of skin conductance corresponding values of skin wetness. For example, the table may be generated by a controlled process in which the skin conductance at different levels of skin wetness is measured.

In another embodiment, a machine learning model (referred to herein as a "skin wetness model") is utilized to calculate the values indicative of the skin wetness based on the second measurements 356. The computer 358 generates feature values based on the values indicative of the skin conductance. For example, one or more of the feature values may include the values of the skin conductance and/or values indicative of measured electrical currents, etc. Optionally, one or more of the feature values are indicative of the temperature and/or humidity levels measured by the second head-mounted sensor 352. The computer 358 then utilizes the skin wetness model to calculate, based on the feature values, a value indicative of the skin wetness. Optionally, the model is generated based on training samples that include feature values generated from pervious measurements taken of one or more users, with head-mounted sensor 354, and labels indicative of the skin wetness levels of the one or more users while the previous measurements were taken. Optionally, the one or more users had known skin wetness levels (e.g., manually determined or determined from image analysis techniques). Optionally, the skin wetness model is generated utilizing a machine learning training algorithm known in the art, such as neural network training algorithm, a regression model training algorithm, and the like.

Various types of values of indicative of skin wetness may be utilized in different embodiments. In one example, values may be binary (i.e., dry or wet). In another example, a numerical value, such as a scale from 1 to 10 may be used. In this example, 1 may be used to indicate completely dry skin (e.g., no perspiration and a dry environment), 5 may be used to denote a state of mild perspiration, and 10 may be used to denote skin that is completely wet (e.g., when exiting a pool).

In some embodiments, the computer 358 calculates an effect of the having the level of skin wetness on the measurements 353. For example, the effect may be one or more values that indicate a change in the intensity of the measured reflections due to the user's skin being wet (compared to intensities that would be expected to be measured had there not been skin). Optionally, the one or more values quantify the change in intensity of the measured reflections. Optionally, the effect of the skin wetness on measurements of reflections is calculated on a regional basis. For example, the one or more values may include multiple values describing the effect of the skin wetness on values measured by different discrete photosensors from among the discrete photosensors belonging to the head-mounted device 342.

In one embodiment, calculating the effect of having a certain level of skin wetness is done utilizing a table that has values that are precomputed values that quantify the effect. In one example, the level of skin conductance is indicative of extent of perspiration, and the computer 358 utilizes a pre-calculated table for estimating the effect of the extent of perspiration on the magnitudes of the reflections. Optionally, the table's pre-calculated values are calculated based on comparing intensities of previous measurements of reflections, from the user's face, measured by the head-mounted device 342 at different times. The previous measurements include a first set measurements of reflections taken when there was no excessive skin wetness, and a second set of measurements of reflections taken when there was skin wetness. Thus, differences between the first and second sets correspond to values of the effect of the interference. In this example, the first set of measurements can serve as a baseline to which different levels of skin wetness may be compared, and thus the effects of the different levels can be quantified and used as values in a lookup table that provides the effect of skin wetness (on values of measurements of reflections) according to its calculated level (based on measurements taken with the head-mounted sensor 354).

In one embodiment, calculating the effect of having a certain extent of an interference (e.g., a certain level of skin wetness) is done utilizing a machine learning-based approach. The computer 358 calculates feature values based on measurements taken by the head-mounted sensor 354 (and optionally additional data, as described below). The computer 358 utilizes a model (referred to herein as an "effect model") to calculate, based on the feature values, one or more values indicative of the effect of the interference. Optionally, the effect model is generated based on samples that are generated from training data that includes previously taken measurements (taken by the head-mounted sensor 354). Optionally, the training data also includes previous measurements of reflections measured by the head-mounted device 342 at the times the previously taken measurement were taken by the head-mounted sensor 354. Optionally, the training data also includes additional data such as values of environmental conditions and/or identification of facial expressions that were expressed while the previously taken measurements were taken by the head-mounted sensor 354. Optionally, each training sample includes feature values generated based one or more of the aforementioned training data types and a label, as explained below.

In one example, one or more of the feature values generated based on measurements that were taken by the head-mounted sensor 354 may be image-based feature values discussed above (when the head-mounted sensor 354 is a camera). In another example, the one or more feature values include values describing the level of skin conductance. In yet another example, one or more feature values are indicative of the extent of the interference (e.g., a value obtained using an approach described above for calculating the extent of an interference).

In some embodiments, the feature values used to calculate the one or more values indicative of the effect of an interference are indicative of environmental conditions (e.g., brightness of the environment, temperature of the environment, etc.).

In one embodiment, labels of training samples used to train the effect model are indicative of the effect of an interference on the measurements of the reflections. Optionally, the effect is determined by comparing first and second measurements of reflections taken at first and second times. The first and second times are selected, such that at the first time, the interference was below a certain level (e.g., dry skin) and at the second time, the interference was above the certain level (e.g., wet skin).

Thus, given measurements taken by the head-mounted sensor 354, the computer 358 can calculate feature values (e.g., indicating the extent of the interference of skin wetness) and use the effect model to calculate values indicative of what effect this has on measurements of reflections measured by the head-mounted device 342. For example, each of the values may indicate a change to the intensity of measured reflections at a certain photosensor. These values may be provided, in turn, to an algorithm that detects facial expressions based on measurements of reflections, as discussed above.

In one embodiment, similarly to the computer 348, the computer 358 may operate the light sources of the head-mounted device 342 according to first and second different schedules responsive to detecting first and second different facial expressions belonging to the facial expressions, being detected.

The following method may be used by systems modeled according to FIG. 5. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting, by a head-mounted device (e.g., the head-mounted device 342), light towards a first region on a user's face, and taking, using discrete photosensors, first measurements of reflections of the light from the first region.

In Step 2, taking second measurements of a second region on the face by a head-mounted sensor (e.g., the head-mounted sensor 354).

In Step 3, calculating a level of skin wetness based on the second measurements taken in Step 2.

And in Step 4, detecting facial expressions of the user based on the first measurements taken in Step 1 and the level of skin wetness calculated in Step 3.

In one embodiment, the head-mounted sensor includes electrodes, the second measurements taken in Step 2 include a signal indicative of level of skin conductance, the calculating of level of skin wetness in Step 3 is based on the signal, and an average rate of taking first measurements in Step 1 is at least ten times higher than an average rate of measuring the signal in Step 2.

In one embodiment, the head-mounted sensor includes a camera, the second measurements taken in Step 2 include images of the second region, the calculating of level of skin wetness in Step 3 is based on analyzing the images, and an average rate of taking the first measurements in Step 1 is at least ten times higher than an average rate of capturing the images in Step 2.

In one embodiment, an average rate of taking the first measurements in Step 1 is at least 10 times higher than an average rate of taking the second measurements in Step 2, and the average rate of detecting the facial expressions in Step 4 is higher than the average rate of taking the second measurements in Step 2.

In one embodiment, the method optionally includes a step of operating the light sources used to take the first measurements in Step 1 according to first and second different schedules responsive to detecting first and second different facial expressions from among the facial expressions.

Another factor that can affect accuracy of detections made based on reflections of light using head-mounted discrete photosensors involves shifts due to positioning of a head-mounted system holding these sensors on the user's head. Each time a user's puts on such a system (e.g., smartglasses with coupled sensors), or even during use in day-to-day activities, the head-mounted system's position can change ever so slightly, compared to previous positions it was in. These slight changes in position, which are referred to herein as "sensor shifts", may affect the patterns of detected reflections, in some embodiments described herein, and thus may need to be accounted for in order to improve the accuracy of detections made based on the measured reflections (e.g., detection of locations of facial landmarks or detection of facial expressions).

Figure 6:
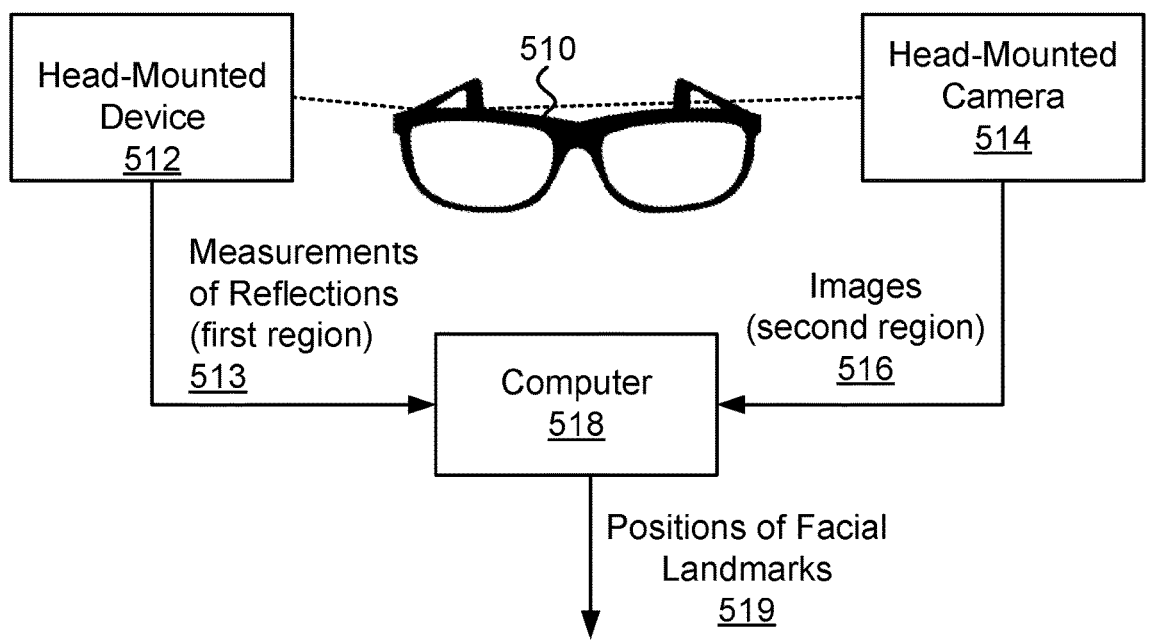
FIG. 6 illustrates an embodiment of a system that detects facial expressions while accounting for sensor shifts.

Some embodiments described herein involve accounting for sensor shifts in order to improve detection of positions of facial landmarks based on measurements of reflections of light using discrete photosensors. FIG. 6 illustrates an embodiment of a system that detects facial expressions. The system includes a head-mounted device 512, a head-mounted camera 514, and a computer 518. Optionally, the head-mounted device 512 and/or the head-mounted camera 514 are coupled to a frame of smartglasses 510, which are configured to be worn on a user's head.

The head-mounted device 512 includes one or more light sources and discrete photosensors. The light sources emit light towards a first region on the user's face. The discrete photosensors, which are spread over more than 2 cm, take measurements 513 of reflections of the light from the first region. Additional details regarding possible configurations for the head-mounted device 512 are provided in the discussion of characteristics of the head-mounted device 342, which in some embodiments, shares similar properties with the head-mounted device 512.

The head-mounted camera 514 captures images 516 of a second region on the face. Optionally, the images 516 are captured at a rate that is lower than a rate at which the measurements 513 are taken. In one example, an average rate at which the measurements 513 of the reflections are taken is at least ten times an average rate at which the images 516 are captured.

In some embodiments, head-mounted camera 514 utilizes a sensor that has more than 100 pixels. In these embodiments, the head-mounted camera 514 may have a lens, and the sensor plane of the head-mounted camera 344 may be tilted by more than 2° relative to the lens plane of the head-mounted camera 514, according to the Scheimpflug principle, in order to capture sharper images.

In some embodiments, the head-mounted device 512 and the head-mounted camera 514 are fixed to a smartglasses frame, such as the frame of the smartglasses 510. Optionally, at least a portion of the first region is located less than 4 cm from one of the user's eyeballs, the second region is located in a known position relative to the first region, and the first and second regions overlap. Alternatively, at least a portion of the first region is located less than 2 cm from one of the user's eyeballs, the second region is located in a known position relative to the first region, and the first and second regions do not overlap and have a minimal distance between their borders below 2 cm.

The computer 518 calculates, based on the images 516, values indicative of a location and/or orientation of the head-mounted device 512 relative to the face. In some embodiments, the values indicative of a location and/or orientation include values indicating the location and/or size of certain facial landmarks in the second region. In some examples, the values may include pixel co-ordinates of landmarks such as an eyebrow, the tip of the nose, a tip of an earlobe, a pupil, etc. For example, the values may include co-ordinates of the left side and the right side of an eyebrow. In other examples, the values may include sizes of facial landmarks, such as the length of an eyebrow (e.g., in pixels) or the length of the nose bridge (in pixels). In yet another example, the values calculated based on the images may include an angle of the lens plane, estimated based on the observed location of one or more facial landmarks (given that the expected location of the head-mounted camera 514 is known).

In some embodiments, the values indicative of the location and/or orientation of the head-mounted device 512 relative to the face are indicative of the change in the location and/or orientation of the head-mounted device 512 relative to the face. For example, the values may indicate a change in location, size, or orientation of certain facial landmarks detected in the images 516 compared to their location, size, or orientation as determined in previously taken images, which were taken by the head-mounted camera 514.

It is to be noted that it is assumed that the relative locations between the head-mounted camera 514 and the head-mounted device 512 are fixed and known (e.g., both are mounted to a rigid head-mounted frame). Therefore, information indicating the location and/or orientation of the head-mounted camera 514 is also indicative of a location and/or orientation of the head-mounted device 512.

Figure 7:
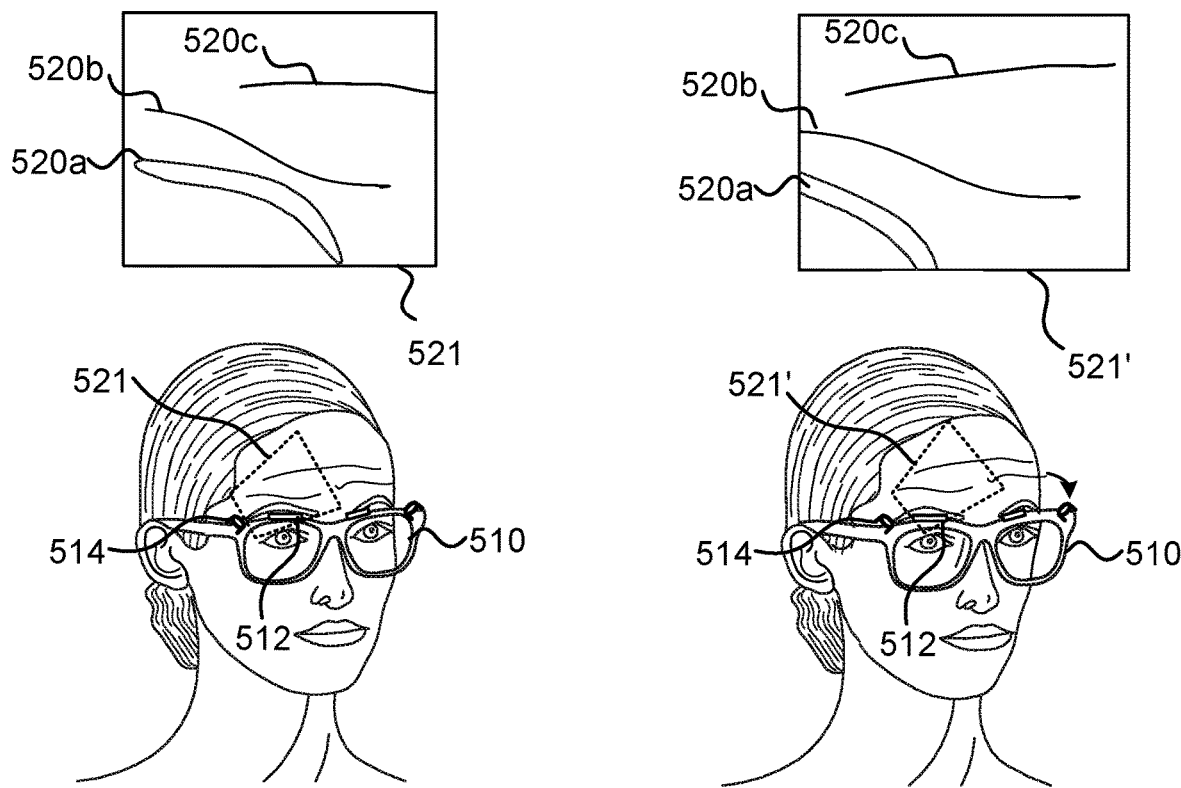
FIG. 7 illustrates how locations of facial landmarks may change in images due to sensor shift.

FIG. 7 illustrates how locations of facial landmarks may change in images due to shifting of a head-mounted device. When the location of the smartglasses 510 shifts (difference between images on the left and right), this causes a change to the location in images of the eyebrow 520a and forehead wrinkles 520b and 520c. The different in the position of the facial landmarks provides indications about the change to the distance and/or orientation of the smartglasses 510 (as well as the head-mounted device 512 and the head-mounted camera 514) relative to the face.

A shift of the photosensors of the head-mounted device 512 relative to the face (sensor shift) can reduce accuracy of detection of the positions of the facial landmarks based on the measurements 513. This reduction in accuracy may occur because measurements by photosensors can be quite sensitive to changes in orientation of the illumination. Thus, slight changes in the illumination by the light sources of the head-mounted device 512 (due to the sensor shift), can lead to large changes in a pattern of reflections from the first region, which are detected by the photosensors of the head-mounted device 512. In order to address such inaccuracies due to sensor shifts, the computer 518 can utilize the values indicative of the location and/or orientation of the head-mounted device 512 relative to the face, which are calculated based on the images 516, as described below.

The computer 518 detects, based on the reflections measured by the head-mounted device 512 (i.e., based on the measurements 513) and the aforementioned values calculated based on the images 516, positions of facial landmarks. Optionally, the detection is performed at an average rate higher than an average rate at which the images 516 are captured. Optionally, the detection is performed utilizing a machine learning-trained model, as described below. Optionally, an average rate at which the reflections are measured is at least 50 times higher than an average rate at which the images are captured, and the average rate at which the facial landmarks are detected is at least 10 times higher than the average rate at which the images are captured. Optionally, the computer 518 also renders an avatar representing the user based on the positions of the facial landmarks using one or more of the approaches known in the art.

In some embodiments, the computer 518 calculates feature values based on the measurements 513 and the values calculated based on the images 516. Optionally, the feature values may include other types of feature values generated based on the images 516, as discussed in the examples below. The computer 518 then utilizes a model (referred to herein as the "landmark detection model") to calculate, based on the feature values, one or more positions of facial landmarks. Optionally, the positions are expressed as distances from reference points such as the location of the head-mounted device 512 and/or positions of certain facial features, such as the eyes or nose.

In one embodiment, the computer 518 generates at least some feature values from the measurements 513 using the values of the measured reflections as features after normalization according to a technique described in Masai, Katsutoshi, et al. "Evaluation of facial expression recognition by a smart eyewear for facial direction changes, repeatability, and positional drift". In another embodiment, the computer 518 generates at least some feature values from the measurements 513 using the values of the measured reflections as features after normalization according to a technique described in Suzuki 2017. In one embodiment, at least some of the feature values are set to the values calculated based on the images 516 which are indicative of a location and/or orientation of the head-mounted device 512 relative to the face.

In addition to feature values describing intensities of measured reflections, the computer 518 may calculate one or more values, based on the images 516, which are indicative of an extent of a certain interference and/or the effect of the certain interference (on the measurements 513), and utilize the one or more values in the detection of the facial landmarks. Optionally, the extent of a certain interference and/or the effect of the certain interference are calculated utilizing the approach used by the computer 348, which is discussed further above.

In a first example, the computer 518 calculates, based on the images 516, a first value indicative of an extent of hair on a first portion of the first region and/or indicative of an effect of the presence of the hair on the first portion of the first region, and utilizes the first value in the detection of the one or more facial landmarks. Optionally, at least one of the feature values is generated based on the first value.

In a second example, the computer 518 calculates, based on the images 516, a second value indicative of an extent of makeup applied over a second portion of the first region and/or indicative of an effect of the presence of the makeup applied over the second portion of the first region, and utilizes the second value in the detection of the one or more facial landmarks. Optionally, at least one of the feature values is generated based on the second value.

In a third example, the computer 518 calculates, based on the images 516, a third value indicative of a change in a level of skin wetness at a third portion of the first region and/or indicative of an effect of the change in the level of skin wetness at the third portion of the first region, and utilizes the third value in the detection of the one or more facial landmarks. Optionally, at least one of the feature values is generated based on the third value.

In a fourth example, the computer 518 calculates, based on the images 516, a fourth value indicative of an extent of skin infection at a fourth portion of the first region and/or indicative of an effect of the skin infection at the fourth portion of the first region, and utilizes the fourth value in the detection of the one or more facial landmarks. Optionally, at least one of the feature values is generated based on the fourth value.

In some cases, when the user is tired, the magnitude of facial movements is reduced compared to their magnitude when the user is alert or refreshed. In addition, the facial expressions expressed while being tired are usually somewhat different than while being fresh. In order to take such information into account when detecting positions of facial landmarks, in some embodiments, the system optionally includes a device configured to measure values indicative of photoplethysmogram signal (PPG signal) of the user. The computer 518 calculates a level of fatigue based on the PPG signal, e.g., by detecting the level of heart rate variability. Optionally, at least one of the following values is used to generate a feature value that is utilized to detect the positions of facial landmarks: the heart rate, the heart rate variability, and the fatigue level.

Generating the landmark detection model involves collection of a labeled training samples. Optionally, each of the labeled training samples includes feature values generated based on measurements taken by the head-mounted device 512 and images taken by the head-mounted camera 514 (which are utilized to calculate feature values, as described above), and a label indicative of positions of one or more facial landmarks. For example, the label may indicate positions of one or more of the following relative to the head-mounted device 512: an eyebrow, the tip of the nose, an edge of the mouth, or a pupil.

In order to better address variability and inaccuracies that may be introduced due to sensor shifts, in some embodiments, training samples are collected when the head-mounted device 512 is at slightly different positions relative to the face. Optionally, training samples from measurements of a user are collected in several rounds, where in each round the head-mounted device 512 is slightly moved. For example, when the head-mounted device 512 is coupled to smartglasses 510, the smartglasses 510 can be worn an removed several times during the process of collecting training data, or moved around during the process (e.g., by having the smartglasses 510 sit on slightly different locations on the nose).

Labels for the training samples may be generated in various ways. In one example, the label may be generated manually (e.g., by a human labeler viewing images of the user and denoting position of facial landmarks image). In another example, the label may be generated based on analysis of the images taken by the head-mounted camera 514 or additional images taken at a different angle (e.g., a front-facing non-head-mounted camera). These images can be analyzed using landmark detection techniques known in the art, such as techniques mentioned in Wang, Nannan, et al. "Facial feature point detection: A comprehensive survey." *Neurocomputing* 275 (2018): 50-65 and/or Khabarlak, et al. "Fast Facial Landmark Detection and Applications: A Survey." *arXiv preprint arXiv:*2101.10808 (2021). Optionally, the training samples includes one or more samples generated based on images of the user.

It is to be noted that in some embodiments the first region (measured with the head-mounted device 512) may include areas that are not part of the second region (which is captured in the images 516). Thus, in some embodiments, positions of facial landmarks may not be may not be depicted in the images 516 (which are of the second region), but may be detectable in an additional source of data used to generate labels (e.g., images captured with a non-head-mounted camera).

The training samples may then be provided to a machine learning training algorithm that trains the landmark detection model based on the training samples. For example, the training algorithm may be a regression algorithm or an algorithm for training neural networks (e.g., a deep learning neural network). Once the landmark detection model is trained, it may be utilized to detect portions of landmarks in unlabeled samples, such as generated based on the measurements 513 and the values calculated based on the images 516.

The following method may be used by systems modeled according to FIG. 6. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1 emitting, by a head-mounted device, light towards a first region on a user's face, and taking, using discrete photosensors, measurements of reflections of the light from the first region. For example, the head-mounted device 512 may be utilize to emit the light and measure the reflections in this step.

In Step 2, capturing, by a head-mounted camera (e.g., the head-mounted camera 514), images of a second region on the face.

In Step 3, calculating, based on the images, values indicative of a location and/or orientation of the device relative to the face.

And in Step 4, detecting, based on the reflections and the values, positions of facial landmarks at an average rate higher than an average rate of capturing the images.

In some embodiments, detecting positions of the facial landmarks is done utilizing a machine learning-based approach that involves generating feature values based on data comprising the images and measurements of the reflections, and utilizing a model for calculating, based on the feature values, values indicative of the positions of the facial landmarks. Optionally, the feature values include one or more feature values based on the values calculated in Step 3. Optionally, one or more of the feature values may be indicative of an interference and/or an effect of the interference.

In one example, the method optionally includes the following steps: (i) calculating, based on the images captured in Step 2, an extent of presence of hair over a portion of the first region; (ii) calculating an effect on the reflections as a result of the presence of hair; and (iii) utilizing the effect in the detecting of the positions of the facial landmarks. Optionally, the feature values utilized to detect the positions of the facial landmarks include a feature value calculated based on the images which is indicative of the effect on the measurements of the reflections due to the presence of the hair over the portion of the first region.

In another example, the method optionally includes the following steps: (i) calculating, based on the images captured in Step 2, an extent of makeup applied over a portion of the first region; (ii) calculating an effect on the reflections due to application of the extent of makeup; and (iii) utilizing the effect in the detecting of the positions of the facial landmarks. Optionally, the feature values utilized to detect the positions of the facial landmarks include a feature value calculated based on the images which is indicative of the effect on the reflections due to the makeup applied to the portion of the first region.

In yet another example, the method optionally includes the following steps: (i) identifying, based on the images captured in Step 2, a change in a level of skin wetness at a portion of the first region; (ii) calculating an effect on the reflections as a result of the change in the level of skin wetness; and (iii) utilizing the effect in the detecting of the positions of the facial landmarks. Optionally, the feature values utilized to detect the positions of the facial landmarks include a feature value calculated based on the images which is indicative of the effect on the reflections due to the change in a level of skin wetness at the portion of the first region.

There are many known automated facial expressions analysis systems that operate based on the principles of the Facial Action Coding System (FACS) that enables deconstructing facial expressions into combinations of specific action units (AU) and their temporal segments that produce the expressions. The automated facial expressions analysis systems usually identify key facial landmarks, from which they detect the facial expressions, quantify the extent of the facial expressions (e.g., large smile vs small smile), and determine temporal properties of the facial expressions (e.g., a smile for 2 seconds vs a smile for 5 seconds).

When analyzing images of the same user, captured by the electro-optical sensor (such as an inward-facing head-mounted camera or a photosensor-based device), the facial expression data is temporally sparse because the maximum rate of changing of the facial expressions according to a classifier and/or a facial expression finite-state machine (FESM) is typically lower than the maximum frame rate of the camera. This difference can be used in order to save power.

In some embodiments, a head-mounted system saves power by reducing the bitrate at which data is read from a head-mounted camera during times at which the next step of a facial expression classifier/FESM is predictable above a predetermined threshold, because the head-mounted camera is expected to stay at the same position relative to the face (so only little changes in the images are expected). When the predictability of the next step of the FESM is below the predetermined threshold, the system may increase the bitrate at which the data is read from the head-mounted camera to detect the (possibly) new state.

Figure 8:
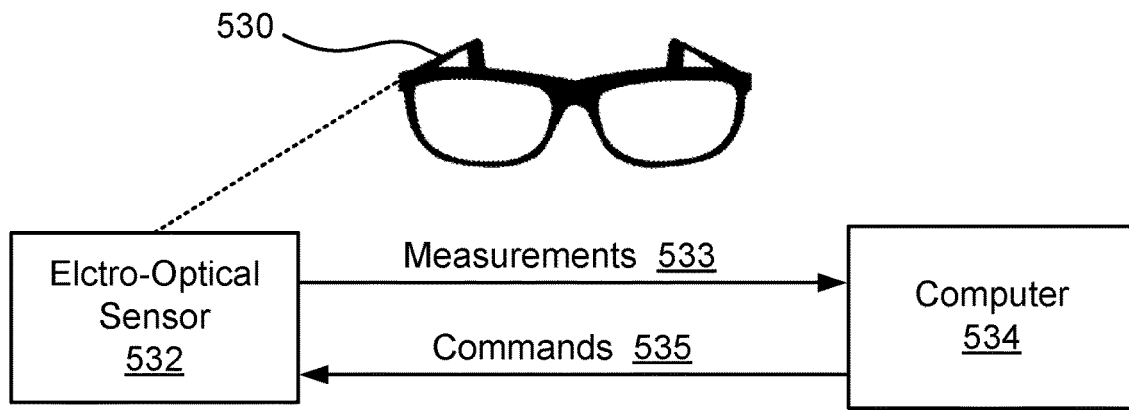
FIG. 8 illustrates an embodiment of a system that detects facial expressions based on measurements of an electro-optical sensor.

FIG. 8 illustrates an embodiment of a system that detects facial expressions based on measurements of an electro-optical sensor. In one embodiment, the system includes a non-contact, head-mounted electro-optical sensor 532 (referred to herein as "electro-optical sensor 532") and a computer 534. Optionally, the electro-optical sensor 532 and/or the computer 534 are coupled to a frame of smartglasses 530.

The electro-optical sensor 532 takes measurements 533 of reflections from a region on a user's head. The measurements 533 are indicative of facial expressions of the user. In one embodiment, the electro-optical sensor 532 comprises an inward-facing head-mounted camera that provides, based on the reflections, images of the region. In this embodiment, the measurements 533 include images of the region on the user's head. In another embodiment, the electro-optical sensor comprises: light sources configured to emit light towards the region, and discrete photosensors, spread over more than 2 cm, configured to measure reflections of the light from the region. In this embodiment, the measurements 533 include measurements of the reflections as detected by the photosensors.

The computer 534 detects, based on the reflections (i.e., based on the measurements 533), a type of facial expression expressed by the user. The type of facial expression can be categorized to one or more of different types of expressions. Optionally, the different types of facial expressions are group that includes at least a type that is considered "neutral facial expressions" and a type that is considered "non-neutral facial expressions".

The computer 534 continues to read the electro-optical sensor 532 at a bitrate that is selected based on the type of facial expression that was detected. Optionally, commands 535 are sent by the computer 534 to the electro-optical sensor 532 in order to facilitate the reading of the electro-optical sensor 532 in the desired bitrate.

In one example, the computer 534 reads the electro-optical sensor 532 at a first average bitrate ($b_1$) when the user expresses a facial expression that is a neutral facial expression (. In another example, the computer 534 reads the electro-optical sensor 532 at a second average bitrate ($b_2$) when the user expresses a facial expression that is a non-neutral facial expression. In these two example, $b_2 > b_1$ (such that data is read at a higher bitrate when a non-neutral facial expression is being expressed by the user compared to a neutral facial expression).

In one embodiment, the group of facial expressions also includes one or more transitional facial expressions. In this embodiment, the computer 534 reads the electro-optical sensor 532 at a third average bitrate ($b_3$) during the transitional facial expressions, where $b_3 > b_1$ (such that data is read at a higher bitrate when a during the transitional facial expression is being expressed by the user compared to a neutral facial expression). Optionally, the bitrate during the transitional facial expressions is higher than the bitrate during the non-neutral facial expressions ($b_3 > b_2 > b_1$). Reading at a higher bitrate during the transitional facial expressions can help the system to detect the new facial expression quickly.

Herein, a "transitional facial expression" is a brief facial expression that is expressed while transitioning from a first facial expression to a second facial expression (i.e., an expression observed on the face some time while the face's muscles are in motion in order to change between the first and second facial expressions).

In some embodiments, in which the electro-optical sensor 532 includes an inward-facing head-mounted camera, the computer 534 may lower the bitrate from $b_2$ to $b_1$ by reading the camera using a higher binning value and/or using a smaller region of interest (ROI) readout.

Binning refers to combining pixel values by the camera, such that the sensor has to read less pixels from the camera because of the reduced resolution. Skipping refers to skipping over certain pixels. Binning and skipping may increase the framerate and optionally also reduce the camera's duty cycle. The image sensor of the camera may support equal and/or different Horizontal and Vertical binning values and/or skipping values, such as 2H×2V binning that combines 4-pixel values (also referred to as binning value equals 4), or 3H×3V binning that combines 9-pixel values (also referred to as binning value equals 9). Binning may be combined with skipping, such as 3H×9V binning plus 3H×9V skipping.

In CMOS-based camera sensors, such as the image sensors that may be used by the head-mounted camera in some embodiments, the term "region of interest" (ROI) may also be known as: window of interest readout, windowing, sub-windowing, region of interest readout, programmable region of interest, area of interest, partial readout window, random pixel access, and direct pixel addressing. In CCD-based camera sensors, the term region of interest may also be known as partial scanning. For "a sensor that supports changing of its ROI", the changing of the ROI is a feature that allows reading only a portion of the pixels that were captured, and by that increasing the readout speed of the ROI, and optionally also reducing the camera's duty cycle. Some imaging sensors also allow multiple ROI readouts in order to simplify the operation of multiple windowing. Sentences of the form of "set the ROI according to a subset of pixels" or "to place the ROI around pixels covering an object refer to setting the coordinates of the ROI to cover the "subset of pixels" or "pixels covering an object", respectively. Herein, pixels are considered to "cover" a region/object if they are able to detect light reflected from that region/object.

In some embodiments, in which the electro-optical sensor 532 includes an inward-facing head-mounted camera, the computer 534 may read images having different sizes when different expressions are expressed. Optionally, the computer 534 may read from the camera images having a first average size ($size_1$) when the user expresses a facial expression from among the neutral facial expressions, read from the camera images having a second average size ($size_2$) when the user expresses a facial expression from among the non-neutral facial expressions, where $size_2 > size_1$. Optionally, images of $size_2$ have a higher resolution than images of $size_1$. Optionally, the computer 534 controls resolution of the images utilizing at least one of binning and windowing.

In one embodiment, image size is proportional to color depth, such that the color depth read from the camera when the user expresses a non-neutral facial expression is higher compared to the color depth read from the camera when the user expresses a neutral facial expression. Optionally, color depth expresses either the number of bits used to indicate the color of a single pixel, or the number of bits used for each color component of a single pixel.

In one embodiment, the group of facial expressions identified by the computer 534 also includes transitional facial expressions, and the computer 534 reads from the camera images having a third average size ($size_3$) during the transitional facial expressions, where $size_3 > size_1$.

Figure 9:
FIG. 9 illustrates reading at different bitrates based on a detected facial expression.
Figure 9:
Figure 9:
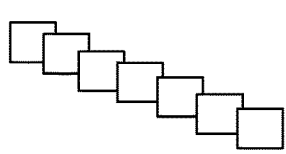
Figure 9:
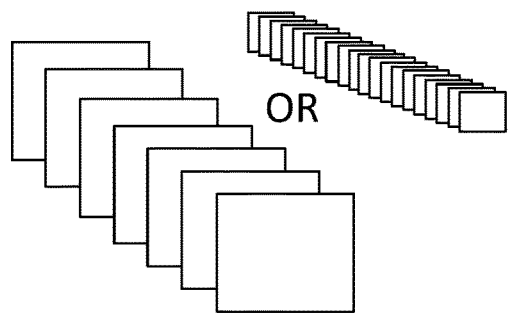

FIG. 9 illustrates reading at different bitrates based on a detected facial expression. On the left side, the detected facial expression is a neutral facial expression, and therefore the camera is read at a low bitrate. On the right side, a non-neutral facial expression is detected, so the camera is read at a higher bitrate. In this illustration, reading at a higher bitrate may be achieved by reading images at a higher framerate or by reading images of a larger size (e.g., higher resolution images).

In some embodiments, in which the electro-optical sensor 532 includes an inward-facing, head-mounted camera that supports changing its ROI, the computer 534 may reduce the bitrate of data read from the camera based on the locations of key facial landmarks. The computer 534 determines locations of key facial landmarks associated with at least some of the non-neutral facial expressions, and sets the camera's ROI to be around at least some of those key facial landmarks. Optionally, the ROI covers less than half of the region in full-resolution images captured by the camera. Determining locations of the facial landmarks can be done utilizing techniques known in the art, which are mentioned above in this disclosure. Reading the ROI, as mentioned above, may reduce the power consumption of the system, and may also improve its performance by increasing the frame rate from the camera.

Once a facial expression is identified and/or a transition to the certain facial expression is identified (from higher resolution images), the ROI can be set to cover relevant facial landmarks, which are known to move when this expression is made and/or when transitioning to another facial expression. Thus, for a short period (e.g., a few tenths of a second), monitoring the user's facial expression can be done more efficiently by reading a small ROI and not a larger ROI (e.g., full resolution images). Once a transition and/or a new facial expression is identified, the images may be read from a larger ROI (or full images) in order to identify a new different set of relevant facial landmarks, according to which a smaller ROI is set and then read.

In one example, in which the group of facial expressions identified by the computer 534 includes transitional facial expressions, the computer 534 determines locations of key facial landmarks associated with a subset of the transitional facial expressions transitioning from the neutral facial expressions. The computer 534 then sets the camera's ROI to be around at least some of said key facial landmarks while the user is in a neutral facial expression from among the neutral facial expressions. Optionally, the ROI in this example covers less than half of the region captured in images taken by the camera.

In another example, in which the group of facial expressions identified by the computer 534 includes transitional facial expressions, the computer 534 determines locations of key facial landmarks associated with a subset of the transitional facial expressions that occur in transitions between certain non-neutral facial expressions and certain neutral facial expressions. The computer 534 then sets the camera's ROI to be around at least some of said key facial landmarks while the user is in a certain non-neutral facial expression selected from the non-neutral facial expressions. Optionally, the ROI in this example covers less than half of the region captured in images taken by the camera.

In yet another example, in which the group of facial expressions identified by the computer 534 includes transitional facial expressions, the computer 534 determines locations of key facial landmarks associated with a subset of the transitional facial expressions that occur in transitions between certain non-neutral facial expressions and other non-neutral facial expressions belonging to the non-neutral facial expressions. The computer 534 then sets the camera's ROI to be around at least some of said key facial landmarks while the user is in a certain non-neutral facial expression selected from the certain non-neutral facial expressions. Optionally, the ROI in this example covers less than half of the region captured in images taken by the camera.

In order to further optimize the system's performance, in some embodiments, in which the electro-optical sensor 532 includes an inward-facing, head-mounted camera that supports changing its ROI, the computer 534 may change the locations of the camera's ROIs, and optionally also the binning of the ROIs, according to the progression of the facial expression being tracked. For example, to infer the extent of a happy smile from the edges of the eyes, it may be enough to set specific windows on the skin wrinkles at the edges of the eyes. This is possible with a head-mounted camera because the camera stays at essentially the same position relative to the head, and the wrinkles are at the same locations for the same kind of smile of the same person. For example, before smiling the computer 534 can lower the image resolution at the edges of the eyes, when the smile begins, the computer 534 can increase the resolution at the edges of the eyes (optionally as the smile grows the resolution is increased at the edges of the eyes while the resolution is decreased in other regions of the image and/or the face), at the peak of the happiness the computer 534 may further increase the resolution to capture the exact extent of the smile, and when the smile fades the resolution may be reduced. During that time the ROIs are located at the expected locations of the wrinkles, and the resolution is set as needed by an image processing algorithm. For example, just tracking the state of the expression and whether there was a change may require a lower resolution compared to detecting a new state to which the user is transitioning.

In one embodiment, the computer 534 performs the following responsive to the user expressing a happy smiling facial expression, from among the non-neutral facial expressions: determine expected locations, in the images, of skin wrinkles at the edges of the user's eyes while expressing the happy smiling facial expression, and to set the camera's region of interest (ROI) to include at least a portion of said expected locations of the skin wrinkles while the user expresses the happy smiling facial expression.

In another embodiment, the computer 534 performs the following responsive to the user expressing a smiling facial expression, from among the non-neutral facial expressions: determine expected locations, in the images, of the user's oral commissures while expressing the smiling facial expression, and to set the camera's region of interest (ROI) to include an expected location of at least one of the oral commissures while the user expresses the smiling facial expression.

In yet another embodiment, the computer 534 performs the following responsive to the user expressing an angry facial expression, from among the non-neutral facial expressions: determine expected locations, in the images, of the user's lips while expressing the angry facial expression, and to set the camera's region of interest (ROI) to be around at least a portion of an expected location of the lips while the user expresses the angry facial expression.

In some embodiments, the computer 534 detects a type of facial expression being expressed utilizing a real-time facial expression finite-state machine that is implemented utilizing at least one of the following: a neural network, a Bayesian network, a rule-based classifier, a support vector machine, a hidden Markov model, a deep learning model, and a deep sparse autoencoder.

The real-time facial expression finite-state machine (FESM) may have different configurations and implementations. The FESM may be implemented explicitly as state machine, or implicitly, for example by one or more Neural Networks, Convolutional Neural Networks, Bayesian Networks, Rule-Based Classifiers, Support Vector Machines, Hidden Markov Models, Deep Learning Models, and Deep Sparse Autoencoders. A key issue in implementing the FESM implicitly is having the ability to provide in real time an indication indicative of the state of the user, which enables the computer 534 to adjust the parameters of the camera as disclosed in this embodiment.

The following is a non-limiting example of a possible implementation of the FESM using a finite-state machine that is a simplified version of a Hidden Markov Model. The electro-optical sensor 532, in this example, includes an inward-facing head-mounted camera that captures, based on the reflections, images of the region on the user's face. The features for the facial expression recognition are extracted using Active Shape Models, and a Support Vector Machine (SVM) classifier performs the facial expression recognition at each state. More specifically, the temporal segmentation may include a FESM with a start state, a set of accept states, and a transition function that may be implemented by a state transition table. Assuming an emotional facial expression starts from a neutral facial expression, transitions to a peak expression, and goes back to the neutral state, then the FESM may have two accept states: neutral and emotional state (referred to as apex). For example, when the accept state is the neutral state, the FESM may accept an input video sequence including a cycle of temporal phases from neutral, onset, apex, and offset to the neutral state. And when an apex is an accept state, the FESM may accept an input video stream for facial expression recognition. The FESM may use various logics for transitions between the states, such as a score between successive frames that counts the number of dynamic features detected in the image (e.g., by Lucas-Kanade's optical flow vectors), and an accumulated score between states (e.g., from neutral to apex state). The feature extraction may be implemented using Active Shape Models to each frame in video sequences, and facial features (fiducial points) may be extracted to represent facial geometry from the Active Shape Models landmarks. The classifier may be based on a SVM (for example with Radial Basis Function kernel), trained with the parameters comprising the displacement of the normalized geometrical features between neutral and apex expression. To recognize the emotions per apex frame, the system may check in video sequences if the current frame is on neutral or apex; if the current state is on neutral, then it saves current features as neutral features and keep up-to-date neutral features during neutral states; if the current state is on apex, the is extracts apex features and creates a new feature vector as relative displacement between neutral and apex features. When meeting an apex state during a single facial expression, the feature vector is fed into the SVM to classify the facial expression, and a final decision for the facial expression in the temporal segment may be determined by the majority of facial expressions counted in the apex states.

In some embodiments, the electro-optical sensor 532 includes: light sources configured to emit the light, and discrete photosensors configured to measure the reflections. Optionally, the discrete photosensors are spread over more than 2 cm. Herein, a "photosensitive sensor" refers to a sensor suitable to measure the amount of light reaching the sensor (according to one or more of the disclosed embodiments). Examples of photosensitive sensors include photodiodes, photodetectors, photosensors, active-pixel sensors, CMOS sensors, and CCD sensors. A photosensitive sensor may be utilized just to measure light, or have a bi-directional characteristic with the ability to emit light and to measure reflections, as further described below.

Figure 12:
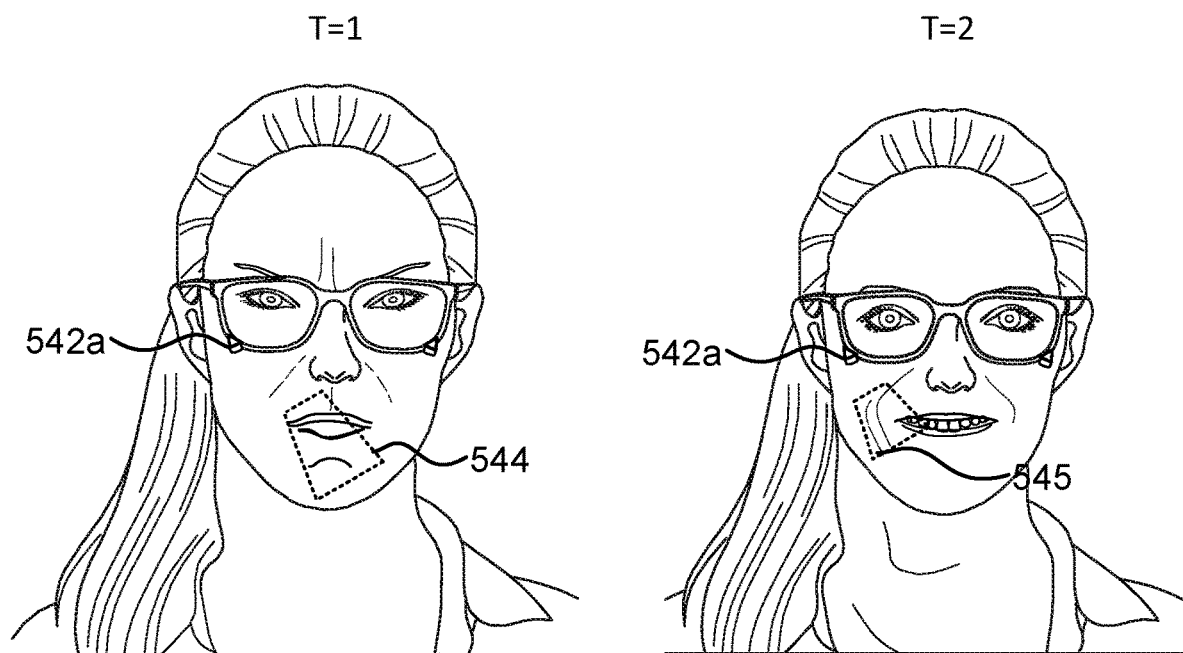
FIG. 12 illustrates dynamic changing of ROIs at different times when movements at different regions occur.

The relevancy of different light sources during expression of different facial expressions, may be different. For example, with different facial expressions, different regions of the face may become important (e.g., as illustrated in FIG. 12 further below). In order to save power, the system may select the more relevant light sources for the specific facial expression. In one example, the computer 534 operates the light sources according to first and second different schedules responsive to detecting first and second different facial expressions belonging to the non-neutral facial expressions. In another example, the computer 534 operates the light sources according to a first schedule responsive to detecting a neutral facial expression and operates the light sources according to a second schedule responsive to detecting a non-neutral facial expression. Optionally, according to the first schedule, a certain light source from among the light sources operates for a longer duration and/or with stronger intensity compared to its operation according to the second schedule. Optionally, according to the first schedule, a certain light source from among the light sources does not operate at all (i.e., does not emit light), while it operates and emits light according to the second schedule.

In one embodiment, the electro-optical sensor 532 includes: at least two Light Emitting Diodes (LEDs) having a bi-directional characteristic with the ability to emit the light and to measure the reflections. Optionally, each of the at least two LEDs is sensitive to wavelengths equal to or shorter than the predominant wavelength it emits. Optionally, each of the at least two LEDs provides illumination when a forward voltage is applied to its electrical terminals, and acts as photodetector/photodiode for example by the following three steps: (i) apply a reverse voltage pulse for a short duration, (ii) discharge the LED's capacitance immediately afterwards, and (iii) measure the voltage across the LED to determine how much discharge of capacitance took place after a certain time. This technique is well known in the art and is further explained in publications such as (A) Akşit, Kaan, Jan Kautz, and David Luebke "Gaze-Sensing LEDs for Head Mounted Displays" arXiv preprint arXiv:2003.08499 (2020), and (B) Dietz, Paul, William Yerazunis, and Darren Leigh "Very low-cost sensing and communication using bidirectional LEDs" International Conference on Ubiquitous Computing, Springer, Berlin, Heidelberg, 2003.

In some embodiments, the rate at which the electro-optical sensor 532 is read may be influenced by additional signals that may warrant increasing or decreasing the bitrate (e.g., by changing the resolution and/or frequency of measurements).

Many emotional states cause an increase in the heart rate, thus the computer 534 may increase the bitrate at which the electro-optical sensor 532 is read in order to improve the accuracy of detecting the facial expressions at the cost of using more power in some configurations. In one embodiment, the computer 534 receives values indicative of the user's heart rate, and determines how to read the electro-optical sensor 532 based on these values. Optionally, the computer 534 reads the electro-optical sensor 532 at the first average bitrate when the heart rate is below a threshold, and reads the electro-optical sensor 532 at the second average bitrate, which is higher than the first average bitrate, when the heart rate is above the threshold.

Movement may also be used to determine how to read the electro-optical sensor 532. For example, until some extent, there is usually a relationship between interesting facial expressions and head movements; thus, in order to save power, the system may increase the rate of measuring the facial expressions when the head movements reach a threshold. In one embodiment, the system includes a head-mounted movement sensor, e.g., an inertial measurement unit (IMU) coupled to the frames of the smartglasses 530). In this embodiment, the computer 534 reads the electro-optical sensor 532 at the first average bitrate when the movements are below a threshold, and reads the electro-optical sensor 532 at the second average bitrate, which is higher than the first average bitrate, when the movements are above the threshold.

The following method may be used by systems modeled according to FIG. 8. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, measuring, by a non-contact head-mounted electro-optical sensor (e.g., the electro-optical sensor 532), reflections from a region on a user's head. The measured reflections are indicative of facial expressions of the user.

In Step 2, detecting, based on the reflections (measured in Step 1), a type of facial expression expressed by the user, which belongs to a group comprising neutral facial expressions and non-neutral facial expressions.

In Step 3, reading the electro-optical sensor at a first average bitrate ($b_1$) when the user expresses a facial expression from among the neutral facial expressions.

And in Step 4, reading the electro-optical sensor at a second average bitrate ($b_2$) when the user expresses a facial expression from among the non-neutral facial expressions, where $b_2 > b_1$.

In one embodiment, the group of facial expression detected in Step 2 comprises transitional facial expressions, and the method optionally includes a step of reading the electro-optical sensor at a third average bitrate ($b_3$) during the transitional facial expressions, wherein $b_3 > b_2 > b_1$.

In some examples described below, the electro-optical sensor used in Step 1 comprises an inward-facing head-mounted camera that provides images of the region by detecting the reflections.

In one example, the method optionally includes the following steps: determining locations of key facial landmarks associated with at least some of the non-neutral facial expressions, and setting the camera's region of interest (ROI) to be around at least some of the key facial landmarks. Optionally, the ROI covers less than half of the region.

In another example, the group of facial expression detected in Step 2 includes transitional facial expressions, and the method optionally includes the following steps: determining locations of key facial landmarks associated with a subset of the transitional facial expressions transitioning from the neutral facial expressions, and setting the camera's region of interest (ROI) to be around at least some of said key facial landmarks while the user is in a neutral facial expression from among the neutral facial expressions. Optionally, the ROI covers less than half of the region.

In yet another example, the group of facial expression detected in Step 2 includes transitional facial expressions, and the method optionally includes the following steps: determining locations of key facial landmarks associated with a subset of the transitional facial expressions that occur in transitions between certain non-neutral facial expressions and certain neutral facial expressions, and setting the camera's region of interest (ROI) to be around at least some of said key facial landmarks while the user is in a certain non-neutral facial expression selected from the non-neutral facial expressions. Optionally, the ROI covers less than half of the region.

In yet another example, the group of facial expression detected in Step 2 includes transitional facial expressions, and the method optionally includes the following steps: determining locations of key facial landmarks associated with a subset of the transitional facial expressions that occur in transitions between certain non-neutral facial expressions and other non-neutral facial expressions belonging to the non-neutral facial expressions, and setting the camera's region of interest (ROI) to be around at least some of said key facial landmarks while the user is in a certain non-neutral facial expression selected from the certain non-neutral facial expressions. Optionally, the ROI covers less than half of the region.

When it comes to tracking facial expression, not all regions of the face carry the same importance; some regions cover facial landmarks whose location correlates with specific facial expressions (and thus these facial landmarks are worth tracking), while other regions lack such informative facial landmarks. Additionally, different facial expressions may be associated with different regions on the face that are worth tracking, since the different facial expression may be characterized by movement of different subsets of facial landmarks. Therefore, some embodiments described herein, involve setting a region of interest (ROI) of a camera used to track facial expression around the more informative regions for a facial expression being expressed at the time. Such selective reading of the camera can optimize system performance by saving power and reducing computations involved in processing the images that are utilized to track the facial expressions.

Figure 10:
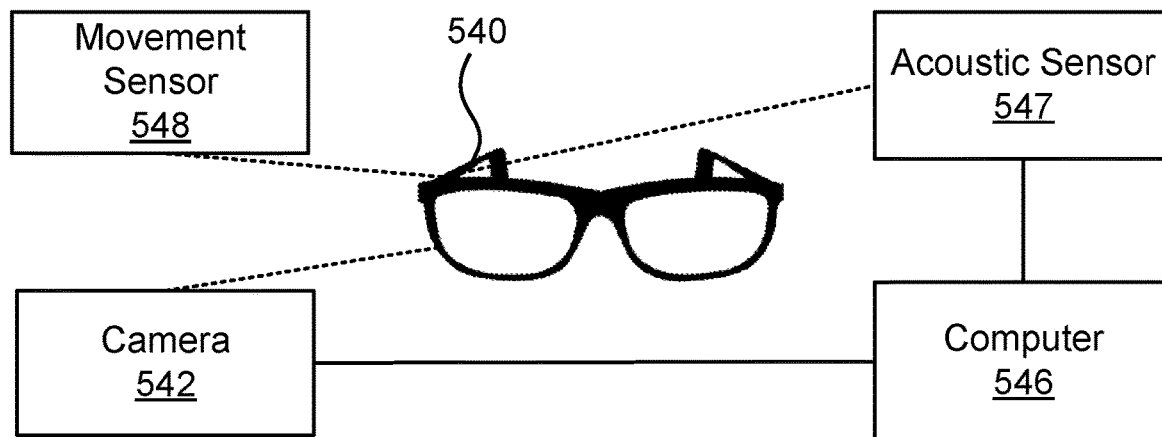
FIG. 10 illustrates an embodiment of a system that utilizes windowing for efficient capturing of facial landmarks.

FIG. 10 illustrates an embodiment of a system that utilizes windowing for efficient capturing of facial landmarks. In one embodiment, the system includes at least an inward-facing head-mounted camera 542 (referred to herein as "camera 542") and a computer 546. Optionally, the system includes additional components such as a head-mounted acoustic sensor 547 or a head-mounted movement sensor 548. Optionally, the camera 542 and/or the computer 546 are coupled to a frame of smartglasses 540. Optionally, the head-mounted acoustic sensor 547 and/or the head-mounted movement sensor 548 are coupled to the frame of the smartglasses 540.

The camera 542 captures images of a region on a user's face, utilizing an imaging sensor that supports changing of its region of interest (ROI). In one embodiment, the camera 542 is physically coupled to a frame configured to be worn on the user's head (e.g., the frame of the smartglasses 540) and the camera 542 is located less than 15 cm away from the user's face.

The computer 546 detects, based on the images captured by the camera 542, a type of facial expression expressed by the user, which belongs to a group comprising first and second facial expressions. For example, the type of facial expression may be indicative of whether the user expressed a neutral facial expression or a non-neutral facial expression. In another example, the type of facial expression may be indicative of whether the user expressed a happy facial expression or a sad facial expression.

Detecting the type of facial expression can be done using approaches known in the art for detecting facial expressions from images. Examples of these approaches are surveyed in Huang, Yunxin, et al. "Facial expression recognition: A survey." *Symmetry* 11.10 (2019): 1189, and Rajan, Saranya, et al. "Facial expression recognition techniques: a comprehensive survey." *IET Image Processing* 13.7 (2019): 1031-1040. Adapting these approaches which typically involve images from non-head-mounted cameras to the case of head-mounted cameras can be done utilizing approaches described in U.S. Pat. No. 9,672,416 titled "Facial expression tracking" to Zhang, and U.S. Pat. No. 10,376,153 titled "Head mounted system to collect facial expressions" to Tzvieli et al., which is incorporated herein by reference.

An identification of the type of facial expression may be used by the computer 546 to set an ROI to be read by the camera 542. In some embodiments, the computer 546 selects the ROI, such that the ROI covers facial landmarks that characterize the facial expression. For example, these landmarks may be expected to move when the facial expression is expressed compared to their location most of the time and/or when a neutral facial expression is expressed.

In one embodiment, responsive to detecting that the user expresses the first facial expression, the computer 546 reads from the camera 542 a first ROI that covers a first subset of facial landmarks relevant to the first facial expression. Additionally, responsive to detecting that the user expresses the second facial expression, the computer 546 reads from the camera 542 a second ROI that covers a second subset of facial landmarks relevant to the second facial expression. In this embodiment, the first and second ROIs are different. Optionally, the size of the overlap in the first and second ROIs is less than 50% the size of the smaller from among the first and second ROIs. Optionally, the first and second ROIs do not overlap. Optionally, each of the first and second ROIs covers less than half of the region captured in the images taken by the camera 542.

Figure 11:
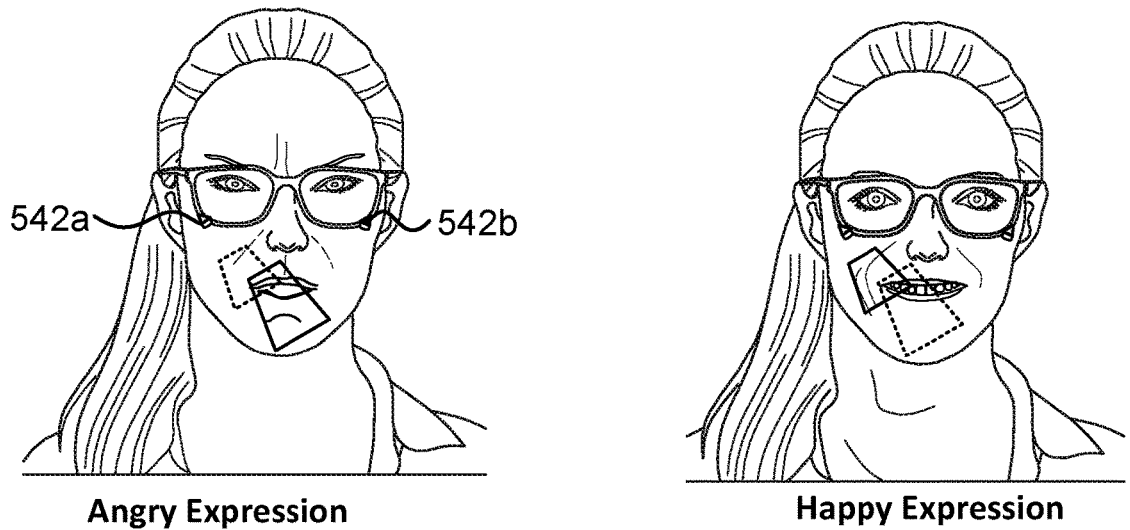
FIG. 11 illustrates the reading of different ROIs when different facial expressions are detected.

FIG. 11 illustrates the reading of different ROIs when different facial expressions are detected. The left portion of the figure illustrates reading of an ROI that is relevant to a detected angry expression (this ROI includes portions of the chin and upper lip). The right portion of the figure illustrates reading of an ROI that is relevant to a detected happy expression (this ROI includes portions of the mouth and cheek).

Selecting subsets of facial landmark that are relevant to a certain type of facial expression can be done by identifying locations of facial landmarks using techniques known in the art, such as techniques mentioned in Wang, Nannan, et al. "Facial feature point detection: A comprehensive survey." *Neurocomputing* 275 (2018): 50-65 and/or Khabarlak, et al. "Fast Facial Landmark Detection and Applications: A Survey." *arXiv preprint arXiv:*2101.10808 (2021). By evaluating locations of facial landmarks in images in which different facial expressions are expressed, relevance scores can be calculated for each landmark (e.g., contours of the mouth, eyes, eyebrows, cheekbones, etc.). For example, a relevance score of a certain facial landmark to a certain facial expression may be proportional to the distance between the location of a certain facial landmark when the certain facial expression is expressed and the average location of the certain facial landmark when a neutral facial expression is expressed or compared to the average location (across all facial expressions of the certain facial landmark). In another example, a relevance score of certain landmark for a certain facial expression is proportional to the drop in performance when the certain landmark is dropped from inputs provided to a facial expression classifier tasked with detecting the certain facial expression. This is akin to testing a facial expression detection model in which the certain facial landmark is not considered. Thus, if the certain facial landmark is important for detecting the certain facial expression, the performance of the classifier will deteriorate. Optionally, dropping a certain facial landmark from the input to the classifier involves dropping additional facial landmarks that are less than a predetermined distance from the certain facial landmark (so they do not compensate for its removal).

In one embodiment, to select the first subset of facial landmarks the computer 546 performs the following: The computer 546 calculates first relevance scores for facial landmarks extracted from a first subset of the images captured by the camera 542. Optionally, the computer 546 selects the first subset of the images based on identifying that the user expressed the first facial expression while those images were taken. The computer 546 then selects a first proper subset of the facial landmarks whose relevance scores reach a first threshold, and sets the first ROI to cover the first proper subset of the facial landmarks. For example, the first ROI may be selected to be a bounding box that covers the locations of the first proper subset of the facial landmarks in the first subset of images. Similarly, to select the second subset of facial landmarks the computer 546 performs the following: The computer 546 calculates second relevance scores for facial landmarks extracted from a second subset of the images captured by the camera 542. Optionally, the computer 546 selects the second subset of the images based on identifying that the user expressed the second facial expression while those images were taken. The computer 546 then selects a second proper subset of the facial landmarks whose relevance scores reach a second threshold, and sets the second ROI to cover the second proper subset of the facial landmarks.

In some embodiments, the computer 546 sets the first and second ROIs based on a pre-calculated function and/or a lookup table that maps between types of facial expressions and their corresponding ROIs. In one example, the ROIs selected according to the aforementioned approach are recorded in a lookup table and/or encoded into a function. In another example, the pre-calculated function and/or a lookup table may be determined by external knowledge (e.g., manually set by an expert).

In some embodiments, the first and/or second ROIs may change dynamically with the movement of at least some of the facial landmarks in the first and second subsets. As the landmark's position in the images changes, the first and/or second ROIs may be shifted, extended and/or shrunk in order to still cover the first and/or second proper subsets of the facial landmarks, respectively. Optionally, the computer 546 detects changes in locations of the facial landmarks in the first and second subsets due to facial movements and/or movements of the camera 542 relative to the face. For example, the computer 546 may utilize techniques known in the art for tracking facial landmarks, described in the references mentioned above. The computer 546 then updates each of the first and second ROIs according to the changes, so they still cover the first and second proper subsets, after the facial and/or camera movements.

In some embodiments, a lack of change in the expressed facial expression can lead the computer 546 to reduce the amount of data that is read from the camera 542 (until a change is detected). In one embodiment, the computer 546 reduces a framerate of reading the first ROI from the camera 542 responsive to detecting that the user expresses the first facial expression for more than a predetermined duration. Optionally, the predetermined duration is 0.5 second or one second.

In another embodiment, a lack of change in the expressed facial expression may cause the computer 546 to further reduce the size of an ROI being read from the camera 542. In one example, the computer 546 reads from the camera 542 a third ROI that covers a third subset of the facial landmarks, which is a proper subset of the first subset of facial landmarks, responsive to detecting that the user expresses the first facial expression for more than a predetermined duration. Optionally, the third ROI is read instead of the first ROI. In one example, the computer 546 selects the third subset as follows. The computer 546 calculates relevance scores for each facial landmark in the first subset of facial landmarks, selects a proper subset of the first subset of facial landmarks whose relevance scores reach a threshold, and sets the third ROI to cover the proper subset of the facial landmarks.

In some embodiments, the imaging sensor of the camera 542 supports changing its binning value, and binning may be used to further save power.

In one embodiment, the imaging sensor supports at least two different binning values for at least two different ROIs, respectively. The computer 546 selects, based on performance metrics of facial expression analysis configured to detect the type of facial expression expressed by the user, first and second resolutions for the first and second ROIs, respectively. For example, the performance metrics may correspond to accuracy of a classifier that is used to detect facial expression in images. The computer 546 then sets different binning values for the first and second ROIs according to the first and second resolutions. Thus, certain more dominant facial landmarks may be samples at lower resolutions without compromising the accuracy of facial expression detection.

In another embodiment, the computer 546 calculates relevance scores for facial landmarks extracted from overlapping sub-regions having at least two different binning values. For example, the sub-regions are subsets of the region, and a relevance score per facial landmark at a binning value increases as accuracy of facial expression detection based on the facial landmark at the binning value increases. Optionally, the relevance also increases as power consumption used for the facial expression detection decreases. The computer 546 sets binning values according to a function that optimizes the relevance scores. For example, the computer 546 may test different combinations of binning values to find an optimal combination. Optionally, this may be done by searching the space of binning values, e.g., utilizing a simulated annealing search approach.

In one embodiment, relevance scores may be increased in proportion to an expected magnitude of movement of the facial landmarks, in order to prefer a higher binning for facial expressions causing larger movements of their respective facial landmarks. For example, the computer 546 may utilize a predictor trained on sequences of movement of facial landmarks, and detect frequent patterns from which the expected magnitudes of movement may be deduced.

In some embodiments, ROIs may be reselected and/or increased in size, in different circumstances. In one example, an ROI that is currently being read is reselected and/or increased following a predetermined period (e.g., after 5 seconds). In another example, an ROI that is currently being read is reselected and/or increased following detection of movement that reaches a certain threshold of one or more facial landmarks that are covered by the ROI. In yet another example, an ROI that is currently being read is reselected and/or increased following receiving an indication of movement of the head, e.g., from the head-mounted movement sensor 548.

Data read from the camera 542 may be utilized by the computer 546 to render an avatar of the user, in some embodiments. Optionally, total power consumed from head-mounted components for a process of rendering an avatar based on the first and second ROIs is lower than total power that would have been consumed from the head-mounted components for a process of rendering the avatar based on images of the region. In one embodiment, the selection of the ROIs takes in account both the accuracy of the rendered avatar and the power consumed by the head-mounted components in the process of rendering the avatar. Optionally, a first ROI that requires significantly less power and results in a slightly less accurate avatar may receive a higher relevance score than a second ROI that take significantly more power that the first ROI and results in just a bit more accurate avatar.

In some embodiment, the system reduces power consumption of its head-mounted components by checking quality of predictions of locations of facial landmarks using a model, and if the locations of the facial landmarks are closer than a threshold to their expected locations, then a bitrate at which the camera is read is reduced. Optionally, the computer 546 identifies that the locations of the facial landmarks are not closer than the threshold to their expected locations, and then increase the bitrate at which the camera is read. Optionally, the model is trained by the computer 546 using sequences of locations of facial landmarks as detected from images read at a high bitrate (e.g., high resolution, high frame rate, and/or without binning).

Movement data and audio data may also be utilized to assist in rendering of avatars. For example, phenome detection based on audio may be utilized to assist in realistic rendering of the mouth of an avatar. Additionally, movement data may assist in determining expressed facial expressions and/or pose and orientation of the face, which can help render a more accurate avatar. In one embodiment, the system includes the head-mounted acoustic sensor 547, which takes audio recordings of the user and the head-mounted movement sensor 548 (e.g., an inertial measurement unit), which measures movements of the user's head. The computer 546 further configured to (i) generate feature values based on data read from the camera 542, the audio recordings, and the movements, and (ii) utilize a machine learning-based model to render an avatar of the user based on the feature values. For example, feature values generated from the data read from the camera 542 may include location of facial landmarks, feature values generated based on the audio may include indications of spoken phenomes, and feature values generated based on movements may indicate types of head movements being performed. In one example, the model was trained based on the following simultaneously taken measurements of the user: previous audio recordings, previous movements, and previous data read from the camera. It is noted that the data read from the camera refers to images captured by the camera 542, wherein the images may be of the region or of a proper subset of the region captured by reading ROIs from the camera.

The following method may be used by systems modeled according to FIG. 10. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, capturing images of a region on a user's face utilizing an inward-facing head-mounted camera comprising a sensor that supports changing of its region of interest (ROI).

In Step 2, detecting, based on the images captured in Step 1, a type of facial expression expressed by the user, which belongs to a group comprising first and second facial expressions.

In Step 3, responsive to detecting that the user expresses the first facial expression, reading from the camera a first ROI that covers a first subset of facial landmarks relevant to the first facial expression.

And in Step 4, responsive to detecting that the user expresses the second facial expression, reading from the camera a second ROI that covers a second subset of facial landmarks relevant to the second facial expression. The first and second ROIs are selected to be different.

In one embodiment, the method optionally includes the following steps: calculating first relevance scores for facial landmarks extracted from a first subset of the images, selecting a first proper subset of the facial landmarks whose relevance scores reach a first threshold, and setting the first ROI to cover the first proper subset of the facial landmarks.

In one embodiment, the method optionally includes the following step: reading from the camera a third ROI that covers a proper subset of the first subset of facial landmarks, responsive to detecting that the user expresses the first facial expression for more than a predetermined duration.

In one embodiment, the image sensor of the camera used in Step 1 supports at least two different binning values for at least two different ROIs, respectively. Optionally, the method includes the following steps: (i) selecting, based on performance metrics of facial expression analysis for detecting the type of facial expression expressed by the user, first and second resolutions for the first and second ROIs, respectively, and (ii) setting different binning values for the first and second ROIs according to the first and second resolutions.

In one embodiment, the user is measured with a head-mounted acoustic sensor configured to take audio recordings of the user and a head-mounted movement sensor configured to measure movements of the user's head. Optionally, the method includes the following steps: (i) generating feature values based on data read from the camera, the audio recordings, and the movements, and (ii) utilizing a machine learning-based model for rendering an avatar of the user based on the feature values.

Some embodiments of the system illustrated in FIG. 10 may be utilized to dynamically track different portions of the face where movement occurs, optionally without detecting the actual facial expression being expressed prior to selection of the relevant ROIs. In these embodiments, the ROIs may change as movements in different sub-regions are detected. For example, in one embodiment, the camera 542 captures images of a region on a user's head utilizing a sensor that supports changing of its region of interest (ROI). The computer 546 detects in a first subset of the images, a first sub-region in which changes due to a first facial movement reach a first threshold. The computer 546 proceeds to read from the camera 542 a first ROI that captures at least a portion of the first sub-region. The computer 546 may then detect, in a second subset of the images, a second sub-region in which changes due to a second facial movement reach a second threshold. And then proceeds to read from the camera 542 a second ROI that covers at least a portion of the second sub-region. Optionally, each of the first and second ROIs covers less than half of the region. Optionally, periods during which the first ROI and the second ROI are read do not overlap.

FIG. 12 illustrates dynamic changing of ROIs at different times when movements at different regions occur. The left portion of the figure illustrates reading, at time T=1, of an ROI that is relevant when movement related to an angry expression is detected (this ROI includes portions of the chin and upper lip). The right portion of the figure illustrates reading of an ROI, at a later time T=2, which is relevant when movement due to happy expression is detected (this ROI includes portions of the mouth and cheek).

In one embodiment, the computer 546 detects changes due to facial movement by: tracking facial landmarks and identifying a sub-region in which the movement of one or more facial landmarks reaches a certain threshold (e.g., a movement of at least a certain distance), and setting an ROI as a shape (e.g., a bounding box) that covers the locations of the one or more facial landmarks. Optionally, the co-ordinates of the shape are set to include a certain sized margin (i.e., even if a facial landmark moves a distance that is less than the certain sized margin, it will remain covered by the ROI). Optionally, the size of the margin is selected in proportion to the extent of movement of the facial landmarks (a larger facial landmark movement leads to selection of a larger margin).

In one example, to select the portion of the first sub-region the computer 546 performs the following: calculate first displacement values for facial landmarks extracted from the first subset of the images, select a first proper subset of facial landmarks whose displacement values reach a first threshold, and set the portion of the first sub-region to cover the first proper subset of the facial landmarks. In this example, a displacement value may refer to a distance to which a depiction of a facial landmark moves in the first subset of the images, e.g., the difference between its location in the first and last images in the subset (in chronological order). Additionally, to select the portion of the second sub-region the computer 546 performs the following: calculate second displacement values for facial landmarks extracted from the second subset of the images, select a second proper subset of facial landmarks whose displacement values reach a second threshold, and set the portion of the second sub-region to cover the second proper subset of the facial landmarks.

In another embodiment, the computer 546 detects changes due to facial movement using an algorithmic approach, such as an optical flow method, or specifically a Lucas-Kanade optical flow method. Utilization of optical flow in detection of facial expression and movement (e.g., detection of action units) is well known in the art. Examples of algorithms that may be utilized by the computer 546 to detect the first and/or second sub-regions in which at least a certain extent of movement occurs are provided in the following references: (i) Sánchez, et al. "Differential optical flow applied to automatic facial expression recognition." *Neurocomputing* 74.8 (2011): 1272-1282; (ii) Sidavong, at al., "Spontaneous Facial Expression Analysis Using Optical Flow Technique", *Modern Sensing Technologies* 5 (2019): 83; (iii) Abdat, et al., "Real time facial feature points tracking with pyramidal lucas-kanade algorithm", *RO-MAN* 2008-*The 17th IEEE International Symposium on Robot and Human Interactive Communication*, IEEE, 2008, and (iv) Verburg, et al., "Micro-expression detection in long videos using optical flow and recurrent neural networks", in 2019 14*th IEEE International Conference on Automatic Face & Gesture Recognition (FG* 2019). Optionally, the computer 546 utilizes one of the aforementioned methods to identify sub-regions in the images in which an extent of movement reaches a threshold (e.g., objects or texture depicted in the sub-region displaces at least to a certain distance and/or at least at a certain velocity). For example, the computer 546 may evaluate a plurality of ROIs covering various sub-regions in the images using an optical flow method in order to determine which of the plurality of ROIs displays movement that reaches a predetermined threshold. Upon detecting such an ROI, the computer 546 may read that ROI from the camera 542. Optionally, the computer 546 identifies facial landmarks and sets the ROIs according to the locations of the facial landmarks.

The process of selecting and reading ROIs can save power and/or improve efficiency of tracking facial expressions. In some embodiments, the processes described above are performed periodically. For example, selection of an ROI that covers a sub-region may be performed every 0.5 seconds or every second. In other embodiments, the selection of ROIs may be triggered by detecting that movement in an ROI that has been read falls below the threshold.

In some embodiments, the rate at which the camera 542 is read may be set according to the extent of facial movement that is detected. In one embodiment, responsive to detecting facial movements below a third threshold for more than a predetermined duration, the computer 546 reduces a framerate of the camera 542. For example, the computer 546 may reduce the framerate from 5 frame per second (fps) to 1 fps when the user watches a movie while expressing a neutral facial expression. In another embodiment, responsive to detecting facial movements above a third threshold for more than a predetermined duration, the computer 546 increases the framerate of the camera 542. For example, the computer 546 may increase the framerate of the camera 542 from 5 fps to 10 fps when the user speaks, because speaking increases the extent of facial movements.

When the image sensor of the camera 542 supports changing its binning value, the computer 546 may read the first and second ROIs with different binning values. In one embodiment, the computer 546 calculates relevance scores for facial expression analysis on at least two resolutions of the first ROI with two different binning values, and sets the binning values according to a function that optimizes the relevance scores. Optionally, a relevance score at a binning value is proportional to accuracy of facial expression detection based on the ROI at the binning value, and inversely-proportional to reduction in image resolution as a result of applying the binning.

In another embodiment, the computer 546 sets a binning value according to a function of a magnitude of a facial movement. For example, in some cases the computer 546 may increase the binning value as a magnitude of the facial movement increases, in order to prefer a higher binning for larger facial movements.

The following is another method may be used by systems modeled according to FIG. 10. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, capturing images of a region on a user's face utilizing an inward-facing head-mounted camera comprising an sensor that supports changing of its region of interest (ROI).

In Step 2, detecting, based on a first subset of the images, a first sub-region in which changes due to a first facial movement reach a first threshold.

In Step 3, reading from the camera a first ROI that covers at least a portion of the first sub-region.

In Step 4, detecting, based on a second subset of the images, a second sub-region in which changes due to a second facial movement reach a second threshold.

And in Step 5, reading from the camera a second ROI that covers at least a portion of the second sub-region; where the first and second ROIs are different.

In one embodiment, the sensor also supports changing its binning value, the method optionally involves reading the first and second ROIs with different binning values.

In another embodiment, the sensor also supports changing its binning value, the method optionally includes the following steps: calculating relevance scores for facial expression analysis on at least two resolutions of the first ROI with two different binning values, and setting the binning values according to a function that optimizes the relevance scores. Optionally, a relevance score at a binning value is proportional to accuracy of facial expression detection based on the ROI at the binning value, and inversely-proportional to reduction in image resolution as a result of applying the binning.

In yet another embodiment, the sensor also supports changing its binning value, the method optionally includes a step of setting a binning value according to a function of a magnitude of a facial movement.

US Patent Application 2019/0223737A1, which is herein incorporated by reference in its entirety and is a previous patent application of the Applicant of this invention, discusses and illustrates in paragraphs 0040-0049, together with their associated drawings, various examples of head-mounted systems equipped with head-mounted cameras, which can be adapted to be utilized with some of the embodiments herein. For example, these paragraphs illustrate various inward-facing head-mounted cameras coupled to an eyeglasses frame, illustrate cameras that capture regions on the periorbital areas, illustrate an optional computer that may include a processor, memory, a battery and/or a communication module, illustrate inward-facing head-mounted cameras coupled to an augmented reality devices, illustrate head-mounted cameras coupled to a virtual reality device, illustrate head-mounted cameras coupled to a sunglasses frame, illustrate cameras configured to capture various regions, such as the forehead, the upper lip, the cheeks, and sides of the nose, illustrate inward-facing head-mounted cameras mounted to protruding arms, illustrate various inward-facing head-mounted cameras having multi-pixel sensors (FPA sensors) configured to capture various regions, illustrate head-mounted cameras that are physically coupled to a frame using a clip-on device configured to be attached/detached from a pair of eyeglasses in order to secure/release the device to/from the eyeglasses, illustrate a clip-on device holds at least an inward-facing camera, a processor, a battery, and a wireless communication module, illustrate right and left clip-on devices configured to be attached behind an eyeglasses frame, illustrate a single-unit clip-on device configured to be attached behind an eyeglasses frame, and illustrate right and left clip-on devices configured to be attached/detached from an eyeglasses frame and having protruding arms to hold the inward-facing head-mounted cameras.

It is noted that the elliptic and other shapes of the regions captured by cameras and other sensing devices in some of the drawings are just for illustration purposes, and the actual shapes of the regions are usually not as illustrated. Furthermore, illustrations and discussions of a camera represent one or more cameras, where each camera may have the same field of view (FOV) and/or different FOVs. A camera includes multiple sensing elements, and the illustrated region captured by the camera usually refers to the total region captured by the camera, which is made of multiple regions that are respectively captured by the different sensing elements. The positions of the cameras in the figures are just for illustration, and the cameras may be placed at other positions.

Various embodiments described herein involve a head-mounted system (HMS) that may be connected, using wires and/or wirelessly, with a device carried by the user and/or a non-wearable device. The HMS may include a battery, a computer, sensors, and a transceiver.

FIG. 13A and FIG. 13B are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, and/or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

As used herein, references to "one embodiment" (and its variations) mean that the feature being referred to may be included in at least one embodiment of the invention. Separate references to embodiments may refer to the same embodiment, may illustrate different aspects of an embodiment, and/or may refer to different embodiments.

Sentences in the form of "X is indicative of Y" mean that X includes information correlated with Y, up to the case where X equals Y. Sentences in the form of "provide/receive an indication (of whether X happened)" may refer to any indication method.

The word "most" of something is defined as above 51% of the something (including 100% of the something). Both a "portion" of something and a "region" of something refer to a value between a fraction of the something and 100% of the something. The word "region" refers to an open-ended claim language, and a camera said to capture a specific region on the face may capture just a small part of the specific region, the entire specific region, and/or a portion of the specific region together with additional region(s). The phrase "based on" indicates an open-ended claim language, and is to be interpreted as "based, at least in part, on". Additionally, stating that a value is calculated "based on X" and following that, in a certain embodiment, that the value is calculated "also based on Y", means that in the certain embodiment, the value is calculated based on X and Y. Variations of the terms "utilize" and "use" indicate an open-ended claim language, such that sentences in the form of "detecting X utilizing Y" are intended to mean "detecting X utilizing at least Y", and sentences in the form of "use X to calculate Y" are intended to mean "calculate Y based on X".

The terms "first", "second" and so forth are to be interpreted merely as ordinal designations, and shall not be limited in themselves. A predetermined value is a fixed value and/or a value determined any time before performing a calculation that utilizes the predetermined value. When appropriate, the word "value" may indicate a "predetermined value". The word "threshold" indicates a "predetermined threshold", which means that the value of the threshold, and/or the logic used to determine whether the threshold is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to utilize windowing for efficient capturing of facial landmarks, comprising:
an inward-facing head-mounted camera configured to capture images of a region on a user's face utilizing a sensor that supports changing of its region of interest (ROI); and
a computer configured to:
detect, based on the images, a type of facial expression expressed by the user, which belongs to a group comprising first and second facial expressions;
responsive to detecting that the user expresses the first facial expression, read from the camera a first ROI that covers a first subset of facial landmarks relevant to the first facial expression; and
responsive to detecting that the user expresses the second facial expression, read from the camera a second ROI that covers a second subset of facial landmarks relevant to the second facial expression; wherein the first and second ROIs are different.

2. The system of claim 1, wherein the computer is further configured to select the first subset as follows: calculate first relevance scores for facial landmarks extracted from a first subset of the images, select a first proper subset of the facial landmarks whose relevance scores reach a first threshold, and set the first ROI to cover the first proper subset of the facial landmarks.

3. The system of claim 2, wherein the computer is further configured to select the second subset as follows: calculate second relevance scores for facial landmarks extracted from a second subset of the images, select a second proper subset of the facial landmarks whose relevance scores reach a second threshold, and set the second ROI to cover the second proper subset of the facial landmarks.

4. The system of claim 1, wherein the computer is further configured to select the first and second ROIs based on a pre-calculated function and/or a lookup table that maps between types of facial expressions and their corresponding ROIs.

5. The system of claim 1, wherein total power consumed from head-mounted components for a process of rendering an avatar based on the first and second ROIs is lower than total power that would have been consumed from the head-mounted components for a process of rendering the avatar based on images of the region.

6. The system of claim 1, wherein the system further comprises a head-mounted acoustic sensor configured to take audio recordings of the user and a head-mounted movement sensor configured to measure movements of the user's head; and the computer is further configured to (i) generate feature values based on data read from the camera, the audio recordings, and the movements, and (ii) utilize a machine learning-based model to render an avatar of the user based on the feature values.

7. The system of claim 1, wherein each of the first and second ROIs covers less than half of the region; and wherein the computer is further configured to detect changes in locations of the facial landmarks in the first and second subsets due to facial movements and/or movements of the camera relative to the user's face, and to update each of the first and second ROIs according to the changes.

8. The system of claim 1, wherein the sensor further supports at least two different binning values for at least two different ROIs, respectively, and the computer is further configured to (i) select, based on performance metrics of facial expression analysis configured to detect the type of facial expression expressed by the user, first and second resolutions for the first and second ROIs, respectively, and (ii) set different binning values for the first and second ROIs according to the first and second resolutions.

9. The system of claim 1, wherein the sensor further supports changing its binning value, wherein the computer is further configured to calculate relevance scores for facial landmarks extracted from overlapping sub-regions having at least two different binning values; wherein the sub-regions are subsets of the region, and a relevance score per facial landmark at a binning value increases as accuracy of facial expression detection based on the facial landmark at the binning value increases and power consumption used for the facial expression detection decreases; and set the binning values according to a function that optimizes the relevance scores.

10. The system of claim 9, wherein the computer is configured to increase the relevance scores in proportion to an expected magnitude of movement of the facial landmarks, in order to prefer a higher binning for facial expressions causing larger movements of their respective facial landmarks.

11. The system of claim 1, wherein the camera is physically coupled to a frame configured to be worn on the user's head, the camera is located less than 15 cm away from the user's face, and the computer is further configured to render an avatar of the user based on data read from the camera.

12. The system of claim 11, wherein the system is further configured to reduce power consumption of its head-mounted components by checking quality of predictions of locations of facial landmarks using a model, and if the locations of the facial landmarks are closer than a threshold to their expected locations, then a bitrate at which the camera is read is reduced.

13. The system of claim 12, wherein the computer is further configured to identify that the locations of the facial landmarks are not closer than the threshold to their expected locations, and then increase the bitrate at which the camera is read.

14. A method comprising:
capturing images of a region on a user's face utilizing an inward-facing head-mounted camera comprising a sensor that supports changing of its region of interest (ROI);
detecting, based on the images, a type of facial expression expressed by the user, which belongs to a group comprising first and second facial expressions;
responsive to detecting that the user expresses the first facial expression, reading from the camera a first ROI that covers a first subset of facial landmarks relevant to the first facial expression; and
responsive to detecting that the user expresses the second facial expression, reading from the camera a second ROI that covers a second subset of facial landmarks relevant to the second facial expression; wherein the first and second ROIs are different.

15. The method of claim 14, further comprising: calculating first relevance scores for facial landmarks extracted from a first subset of the images, selecting a first proper subset of the facial landmarks whose relevance scores reach a first threshold, and setting the first ROI to cover the first proper subset of the facial landmarks.

16. The method of claim 14, wherein the sensor further supports at least two different binning values for at least two different ROIs, respectively; and further comprising (i) selecting, based on performance metrics of facial expression analysis for detecting the type of facial expression expressed by the user, first and second resolutions for the first and second ROIs, respectively, and (ii) setting different binning values for the first and second ROIs according to the first and second resolutions.

17. The method of claim 14, further comprising reducing power consumption of head-mounted components related to the camera by checking quality of predictions of locations of facial landmarks using a model, and if the locations of the facial landmarks are closer than a threshold to their expected locations, then reducing bitrate at which the camera is read.

18. A non-transitory computer readable medium storing one or more computer programs configured to cause a processor based system to execute steps comprising:
  capturing images of a region on a user's face utilizing an inward-facing head-mounted camera comprising a sensor that supports changing of its region of interest (ROI);
  detecting, based on the images, a type of facial expression expressed by the user, which belongs to a group comprising first and second facial expressions;
  responsive to detecting that the user expresses the first facial expression, reading from the camera a first ROI that covers a first subset of facial landmarks relevant to the first facial expression; and
  responsive to detecting that the user expresses the second facial expression, reading from the camera a second ROI that covers a second subset of facial landmarks relevant to the second facial expression; wherein the first and second ROIs are different.

19. The non-transitory computer readable medium of claim 18, further comprising: calculating first relevance scores for facial landmarks extracted from a first subset of the images, selecting a first proper subset of the facial landmarks whose relevance scores reach a first threshold, and setting the first ROI to cover the first proper subset of the facial landmarks.

20. The non-transitory computer readable medium of claim 18, wherein the sensor further supports at least two different binning values for at least two different ROIs, respectively; and further comprising (i) selecting, based on performance metrics of facial expression analysis for detecting the type of facial expression expressed by the user, first and second resolutions for the first and second ROIs, respectively, and (ii) setting different binning values for the first and second ROIs according to the first and second resolutions.

* * * * *